US008150750B2

(12) United States Patent
Ray

(10) Patent No.: US 8,150,750 B2
(45) Date of Patent: Apr. 3, 2012

(54) SYSTEMS AND METHODS FOR MANAGING EXPERT CONTENT

(76) Inventor: Subhransu K. Ray, Moraga, CA (US)

(*) Notice: Subject to any disclaimer, the term of this patent is extended or adjusted under 35 U.S.C. 154(b) by 126 days.

(21) Appl. No.: 12/477,847

(22) Filed: Jun. 3, 2009

(65) Prior Publication Data

US 2009/0299812 A1    Dec. 3, 2009

Related U.S. Application Data

(60) Provisional application No. 61/058,463, filed on Jun. 3, 2008.

(51) Int. Cl.
*G06Q 40/00* (2006.01)
(52) U.S. Cl. ............................................. 705/35; 705/40
(58) Field of Classification Search ................ 705/10–44
See application file for complete search history.

(56) References Cited

U.S. PATENT DOCUMENTS

| 6,003,021 | A | * | 12/1999 | Zadik et al. | 706/47 |
| 6,223,165 | B1 | * | 4/2001 | Lauffer | 705/7.13 |
| 6,523,010 | B2 | * | 2/2003 | Lauffer | 705/7.14 |
| 6,584,445 | B2 | * | 6/2003 | Papageorge | 705/3 |
| 7,249,045 | B2 | * | 7/2007 | Lauffer | 705/7.13 |
| 7,668,735 | B2 | * | 2/2010 | Grace et al. | 705/2 |
| 2007/0250343 | A1 | * | 10/2007 | Sohal | 705/2 |
| 2010/0153131 | A1 | * | 6/2010 | Grace et al. | 705/2 |

* cited by examiner

*Primary Examiner* — Frantzy Poinvil
(74) *Attorney, Agent, or Firm* — Knobbe Martens Olson & Bear, LLP

(57) ABSTRACT

Systems and methods for managing consultation requests to communities of experts comprising receiving consultation requests, receiving responses to consultation requests, and compensating experts for their responses with fractional ownership in a value-added investment vehicle based at least in part on the value of those responses.

28 Claims, 12 Drawing Sheets

NEW MEMBER FORM

Name
Address
City — State
Country
Postal Code
Email

1006

Practice — 1001
Interests:
Referrals
Opinions
Surveys
IVI
Social

1002

Upload CV — 1003
Upload/Link Pubs — 1004

Funding Sources:

NEW CLIENT FORM — 1101

CONTACT INFO

BILLING PLAN — 1102
- ● Per Query
- ● Per Results
- ○ Bulk Plan A
- ○ Bulk Plan B
- ○ Custom

PAYMENT PLAN — 1103
- ● $ U.S.
- ○ Security

AFFILIATED ENTITIES — 1104

FIG. 11

QUERY FORM (dynamic, based on status of submitter)

Question ⎯⎯⎯⎯⎯⎯⎯⎯ 1201

[Add Doc] [Add Options] [Add Tags]

[Add Question]

Audience: — 1202
- ☐ Individuals
- ☐ Geography
- ☐ Specialty
- ☐ All

[Add Factor]

Send Anonymously — 1203

☒ Deadline — 1204

Send On — 1205

FIG. 12

SYSTEMS AND METHODS FOR MANAGING EXPERT CONTENT

CROSS-REFERENCE TO RELATED APPLICATIONS

This application claims priority to provisional application Ser. No. 61/058,463, filed on Jun. 3, 2008.

BACKGROUND OF THE INVENTION

1. Field of the Invention

The present disclosure and claims relate generally to the fields of communications, networked systems, financial systems and more particularly to novel systems and methods for distributing information among specialists, transforming collective knowledge into fungible financial commodities, and distributing fungible financial commodities in novel ways, including according to an intellectual contribution.

2. Description of the Related Art

The pharmaceutical and medical device industries currently rely upon several models for knowledge gathering from physicians, including individual experts, small focus groups, and larger scale survey models. In these models, an entity seeking information faces costs associated with identifying suitable experts, assembling proper panels, and analyzing any results. Also, models involving smaller pools of experts may be efficient but may not reflect the broader opinion of all end-users. For example, in addition to the statistical challenges presented by the use of small groups or individuals, experts participating in this way are more likely to provide opinions that they believe will curry favor with the known or assumed sponsor of the survey.

While a large survey may be more readily structured to avoid statistical anomalies and the large size may hide member bias, large panels may suffer from a dilution of expertise. Also, although this effect can be seen with all of the models, large panels may be particularly vulnerable to superficial or incomplete responses because larger panels are even less likely to provide time-constrained physicians and experts some of the inducements, such as networking or prestige, that smaller panels or individual consulting arrangement might provide.

For these and other reasons, receiving useful feedback from experts can be expensive and difficult. Yet, accessing expertise is increasingly useful, not least because experts are increasingly specialized while market advances and developments are increasingly affected by interactions among diverse domains and diverse specialties within a domain.

Effective solicitation and analysis of responsive survey feedback is particularly important in sectors such as biotechnology and pharmaceuticals, at least in part because the members of the survey panels are both the target market (or strong influencers of the target market) and experts with knowledge or insight into the properties of the products in question. Proper acquisition and analysis of information can lead to benefits such as appropriate market tailoring, improved branding and market penetration upon product launch, and a more efficient use of limited R&D and marketing resources.

There are several internet-based companies that collect data and information from registered physicians through the use of query-based software and hardware (e.g., Sermo, Epocrates, Leerink Swann, and Gerson Lehrman Group). Such entities pay registered experts when those experts participate in a survey, generally without regard to the quality or accuracy of the information provided and without reflecting the ongoing or future value of that information to the recipient or to the market. In addition, there are various industry, academic, professional, and regulatory guidelines that presently restrict the interaction and direct financial relationships between physicians and the medical industry.

The biotechnology and pharmaceutical industries and medical professional, as well as other industries and associated experts, would benefit from alternative systems and methods for operating. It would be useful to provide an incentive to physicians sufficient to induce them to devote the time, attention, and effort necessary to provide quality feedback and answers to questions. Medical experts and others who possess highly desirable knowledge would benefit from a mechanism that allowed them to efficiently maintain ownership of or benefit directly from their own expertise. Because the value of such information can be amplified by aggregating it, it would also be advantageous to be part of an organization that equitably and efficiently leveraged the group's collective expertise. It can also be beneficial to an expert if expertise is not only disseminated for a pre-defined fee, but is instead valued at least in part by the market value of the use to which it is put, especially if a mechanism for doing so does not run afoul of the ethical, legal, and logistical barriers that exist. If those with expertise are better motivated to provide more and better information, then consumers of that information will be rewarded by access to it and will benefit from new systems and methods for interacting with these new organizations of experts and for participating in the motivational compensation systems.

SUMMARY OF THE INVENTION

This disclosure describes embodiments of systems and methods which, through the unique use of computing systems employing interconnected hardware and software, transform grouped expertise into a fungible financial commodity.

This disclosure describes embodiments of systems and methods which may support the formation of groups of experts, enable third parties and group members to benefit from the expertise of individual members and the newly created collective intelligence, transform the collective intelligence into market positions, and/or compensate experts based on the value of their contribution to the group intelligence, on the impact of their contribution in commercial markets, or on other novel factors.

Some disclosed embodiments enable large scale commoditization of grouped physician intellect and transformation of intellectual subject matter contributions into ownership of equity positions. Some enhance the accuracy or utility of information gathered from experts, such as information from physicians regarding research, marketing, development, and post market analysis of pharmaceutical or medical device products. Some embodiments are investment vehicles that rely at least in part on expert information or that are used to compensate experts for providing their expertise. Some embodiments allow for the dissemination of expertise and the compensation of experts without violating conflict of interest issues such as those inherent in many industry-expert interactions.

The present invention includes a novel, and in one embodiment, tripartite system which uniquely serves at least four, currently unmet needs. The invention includes the concept wherein the combined knowledge of a networked-community of physicians, through use of interconnected computer devices, can be directly and rapidly physically transformed into a pooled intellectual commodity. This is then again advantageously converted into equity shares of a participant-owned, actively managed financial commodity or security. It will be understood that Physicians are merely one example of a community of experts to which the invention may apply. Though described in exemplary fashion in the context of physician experts, the invention is not limited thereto.

The tripartite system structure comprises three independently executed but interconnected units:

1. A networked, comprehensive, "invested" multi-specialty physician database (NPD—Networked Physician Database) communicating information and opinion via a central web portal and interconnected computer devices. NPD members may advantageously be paid in vested equity shares of an Internal Investment Vehicle commodity (see below) for providing consultation services to external clients. NPD members may be connected to one another, the Data Query Service, and the Internal Investment Vehicle via several hardware devices including, but not limited to, secure internet based web portal interface, handheld mobile devices, and wireless communication devices. This will allow rapid internal and external communication, with the ability to obtain and deliver split-second physician-opinion information.

a. Registered entry criteria of the NPD that may be cataloged, collated, and stratified by the secure computer devices may include but not be limited to:

Specialty areas of training, areas of board certification, years in practice, matriculated training program(s), sex, age, race, practice type (academic vs. private, group vs. solo, multispecialty vs. single specialty, managed care vs. PPO, hospital vs. community based, surgi-center vs. hospital operating theatre, geographic region of practice, geographic region of training, etc.), peer-based entry ranking, participation in prior advisory boards, involvement in pharmaceutical consultation, participation in clinical trials (NIH, pharmaceutical, or investigator sponsored), b. Progressive weighting criteria that will be cataloged, collated, and stratified by secure computer devices for unique adaptive statistical modeling may include but not be limited to:

Updated continuing medical education credits (CME) status, "clicks" on linked clinical and research articles and information provided on the registered trademark central web portal, "hits" received on their posted material and participation on the discussion boards linked on the registered trademark web portal, accuracy on embedded validation questions within provided surveys, consistency on repeated standardized inter-survey questions provided in sequential surveys, ability of the physician to provide predictive value based on his successful predictions on prior surveys, progressive ranking calibration based on continual inter-physician feedback loops, 2. An independent Data Query Service (DQS) that interrogates the NPD and then via unique software provides value-weighted, statistical modeling of the pooled responses. The DQS may advantageously manage access to the NPD from both external clients and the internal investment vehicle (IIV). In addition to the unique statistical modeling software, the DQS may be composed of hardware devices and software that manages a secure server to house the physician database, and software that allows fluid communication between internal and external sources.

The DQS can: perform secure registration of new physicians; separate log-in for NPD and client members; house the NPD information as noted in 1a and 1b above; perform high level statistical analysis; manage the creation, collection and evaluation of both internal and external computer based queries; provide secure communication with and within the NPD; provide firewalls to prevent inadvertent client exposure to the NPD; house the information library for peer review manuscripts and articles; manage the discussion boards for physician communication within the NPD; store, collect, and report the financial ownership of individual NPD members; enable peripheral and wireless secure hardware and mobile devices to allow rapid communication of high priority requests, notifications, and the subsequent responses.

The DQS log-in may collect and catalog the physician profile information as delineated previously (specialty, practice type, etc). This may be based on a secure registration site which may require private information such as Federal DEA number (Drug Enforcement Agency), State Medical License Number, Social Security Number (IRS information for payment processing), home address, business address, medical school matriculation (for verification of active medical licensing), etc. The DQS may then perform automated registration verification to validate the identification of each new physician.

The DQS may also allow secure registration of new external clients interested in the pharmaceutical or medical device space; such as pharmaceutical companies, medical device manufacturers, investment banks, venture capitalists, institutional investors, marketing companies, government institutions, hospitals, medical insurance companies. The registration may also allow for entry of particular areas of interest, providing automated updates. The client portal may also allow clients to directly input their own survey queries into a DQS formatted style sheets. Clients may also pose specific questions which may be automatically generated into a statistically modeled query. Additionally, clients may simply provide general questions and then request that an NPD section chief generate appropriate surveys. The DQS will communicate this request in an automated format, converting the client into an anonymous source.

3. An active independently-managed internal financial investment vehicle (IIV) that relies on unique internal access to the NPD via the DQS, and acts to convert the fixed currency of payment-for-services (e.g. dollars) into equity shares of the IIV-commodity. The IIV may advantageously invest exclusively in the biotechnology, pharmaceutical, and healthcare industries based on its unique access to the NPD. The IIV will be also connected to the DQS and thereby the NPD, via hardware devices such as wireless and handheld mobile devices in order to obtain immediate market feedback and physician opinion. Instantaneous communication via multiple seamless hardware interfaces allows for greater efficiency and returns from rapidly evolving open market investment opportunities.

Unmet Need 1—Commoditizing Physician Knowledge

One unique feature of this interconnected platform, that distinguishes it from all previous models, involves the unique format of physician payments for consulting services received from corporate clients. Physicians may be paid not in the traditional form of a fixed currency (e.g. dollars), but instead in equity shares of a created financial investment vehicle (IIV) that itself relies upon the subsequent vested-intellect of the same NPD. This novel interconnected technology, for the first time, allows the physical transformation and commoditization of grouped physician intellect (GPI) on a large scale, while allowing the individual participating physicians to maintain direct equity ownership of this intellect via the IIV. Central to this concept is that the financial vehicle's establishment and growth directly reflects the intellectual value of the established NPD. The GPI of the NPD members, as compiled and interrogated by the DQS, is directly leveraged in open financial markets to obtain enhanced returns in the specific market sectors that specialize and rely upon physician intellect and input—pharmaceutical, healthcare, biotechnology, and medical marketing. This is the first large scale conversion of grouped physician knowledge directly into a financial commodity, in which the participating physicians maintain equity ownership of their intellectual creations and ideas. Through the establishment of an efficiently-networked, knowledge-based physician community, and with the incentive of personal ownership, the information provided by these physicians will be superior to that accrued by other means, specifically that accrued by paying physicians in a static currency (e.g. dollars).

The inherent value in this method may advantageously be harnessed by the IIV, which may be actively managed by a knowledgeable fund/security manager, specialized in the fields of biotechnology, pharmaceutical industry, and healthcare. The manager may invest the static funds generated by business operations (see below), leveraging his unique access to the NPD, into the financial markets to obtain enhanced returns on investment. The investment vehicle (IIV), which now represents the commoditized physician intellect, and has enhanced growth potential due to the expert and invested opinion of the database members, will become a financial security of which fractionated shares will be dispersed back to the NPD members. Prorated shares (based on an individuals level of survey participation) of this converted security will then become the method of payment to the physicians for the standard business operations of consulting services.

The IIV, through interrogations of the NPD by use of the DQS, may benefit from the "invested" knowledge and opinion of its membership in order to assist in investment decisions. This unique access advantageously provides a competitive advantage which may then be leveraged in the marketplace to enhance financial returns compared to investment vehicles that rely on more traditional methods. Another advantage is that physicians need not make the financial decisions, as they may not be adequately trained to make the best financial choices. The IIV is an independently executed branch of the business entity, and as such, the expertise of selected fund managers will determine final investment decisions. Thus, another novel aspect of this system and method is to allow unique access to the created "invested" physician database, which will provide the marginal competitive advantage.

The NPD members can be rapidly accessed and access each other, through multiple portals including desktop internet, use of specific mobile handheld or other wireless hardware devices to foster rapid communication and instantaneous dissemination of timely information. These hardware devices will be enabled via a trademark secure central portal registration in order to facilitate a unique virtual landscape for conferencing, consulting, and other interactions.

Unmet Need 2—Accurate Physician Responses

One of the primary external revenue streams for this novel platform is the sale of expert knowledge and opinions of the NPD members to external clients in the pharmaceutical, biotechnology, healthcare, investor, and marketing industries. Physicians are the end-users of products developed by pharmaceutical companies. Physicians are also entrusted by patients and secondary payers to make appropriate medical decisions in managing disease states. Therefore, the pharmaceutical industry utilizes physicians in many roles during product development;

Select academic, clinical, and industry experts are chosen to initiate product development.

Clinicians are subsequently recruited to participate in clinical trials.

Physicians are both recruited and targeted during pre-market launch and in subsequent marketing campaigns.

In summary, the expert opinion and knowledge of physicians are vital during all phases of product development. It is clear that physicians, due to their status as end-users, as well as their extensive years of education, training, and clinical experience occupy a unique and extremely valuable position within the pathway of product development—from start to finish. As stated above, the biotechnology and pharmaceutical sectors provide a unique and rare business opportunity in which the end-user customers are also the providers of expert opinions during product development.

The structure of this novel computer- and device-based technology directly addresses these weaknesses by creating a platform of networked invested and committed physicians. The enhanced value of this informational system translates into an ability to increase the charge to external clients for these physician services. The anonymous nature of the queries generated from the DQS, lacking any criteria identifying its origin as either internal (IIV generated) or external (client generated), advantageously provides incentive to physicians to consistently provide accurate and "committed" opinions, regardless of the source.

The novel system and method may automate or partially automate selection of specific physician members in order to provide work-product sought by a client through one or more selection criteria, including, for example, subject matter expertise, practice area, years of experience, age, gender, work schedule, positions held, courses taught, institutional and/or professional affiliations, training, education, publications, and prior opinions, among possibly many others. The novel system and method may also advantageously store work product and index it automatically by one or more identifying criteria such as, for example, completing physician, client, survey, date, title, study, product and/or related subject matter. The system and method may use a relational database system for physician member profiling and work product storage and indexing. Dynamic network page generation with script-based database querying may be used to provide remote, up-to-date access to or secure administrator-based modification of any of the information in the database.

Payment for services rendered whether for external clients or the IIV, is preferably provided as vested shares of the IIV security. This system and method also uniquely allows external clients to provide payment of services as a fractional ownership or royalties in specific products or companies, by depositing these shares directly into the IIV. Due to the pooled nature of the IIV holdings over all subspecialties, it is unlikely that any one holding will influence any individual's practice patterns or expressed opinions. This is yet another pathway by which grouped physicians, on a large community scale, would be able to own equity in their combined intellectual contributions and innovations. In either case, as there is no option to immediately receive payment in the form of currency, participating physicians will be more likely to provide thoughtful and accurate information.

In order to safeguard the integrity of and any proprietary rights in the externally generated queries, as well as to prevent any SEC or Department of Justice violations, all queries may advantageously be analyzed via the DQS in such a way that information and results of external queries will not be accessible to the IIV, only those that are specifically generated by the IIV. Strict security measures may preferably prevent inappropriate access to confidential material by any internal or other external parties. Signed agreements from all physician members may also be obtained to comply with all SEC and FDA rules and regulations, as well as constraints imposed by basic best ethical practices regarding patient care.

The DQS allows high level stratification of the NPD clients based on multiple pre-entry criteria as noted above in 1a. More importantly however, through a novel adaptive active physician profiling software (AAPPS), higher level statistical modeling and weighting ratios can be performed that will allow greater predictive values of future trends than simple data collection methods as noted above in 1b that will help gage the level of exposure and informational value of any individual physician.

The establishment of three independently executed yet symbiotically related components creates synergistic growth via this created model of financial mutualism. Due to the direct ownership of the intellectual commodity, there is a greater likelihood for accurate and pertinent information from the NPD. This facilitates more accurate investment information input into the decision making processes of the IIV. This in turn creates accelerated growth of the IIV, which further kindles physician interest, commitment, and growth in the NPD. With a growing and committed NPD, there will be further increase in revenue from external clients, thereby further increasing the portfolio holdings of the IIV, resulting in even further growth of the NPD. Due to the interconnected structure, the value of any one of these three separate entities will proportionately increase the value of the other two, thereby leading to synergistic growth of the company as a whole.

Unmet Need 3 & 4—Investment Security Utilizing Input of Financially-Committed Experts while Minimizing Conflict-of-Interest Issues.

As stated earlier, physicians occupy a unique place in the healthcare industry in that they are both the end-user customer of pharmaceutical and bio-technology products, but also provide expert input throughout all stages of product development. Currently, on a large community scale, physicians have no way to maintain some level of equity ownership of their expertise and knowledge. There are avenues for individual physicians to co-write patents or share in royalties from product development, but this is generally restricted to a small percentage of the physician community. Through contractual relationships many physician groups participate in, and are highly compensated for corporate sponsored clinical trials. However this reimbursement is a fixed asset and physicians do not hold any further equity ownership. Appropriately, most physicians are reluctant to hold significant shares in companies that make products commonly utilized in their practices, for fear of giving an appearance of conflict of interest. In addition, physicians in various academic centers or practices involved in clinical trials are restricted in the specific stocks they can own. Today's social and legal environment increasingly frowns upon direct financial interaction between pharmaceutical companies and individual physicians. In fact the AMA has suggested practice guidelines that significantly restrict the exposure to monetary rewards including gifts, honoraria, and advisory board fees. PHRMA guidelines also restrict the amount and types of physician remuneration in order to avoid product bias. Thus, in general, though physicians may have a good understanding of the relative merits of the various companies in the industry, they are unable to benefit from the values of equity ownership.

The creation of an investment vehicle that utilizes the expert opinion of its physician members to assist in investment decisions, allows doctors to maintain an equity ownership in their intellect. Furthermore, by forming a pooled, community-shared financial commodity, there is no direct corporate ownership of one company's equity by any one individual. This dilution of individual knowledge into a pooled financial ownership will allow physicians as a group to own equity in their expertise. Additionally, if certain pharmaceutical industry clients wish to establish an equity sharing partnership with physician groups for the purposes of product innovation or development, the proposed system and method will allow these clients to deposit these equity shares into the pooled vehicle rather than individual physicians. This advantageously thereby creates discrete barriers to minimize conflict of interest scenarios, while still allowing physicians to realize the growth potential of their intellect. Both sides of the interaction would benefit from this relationship.

Through pre-entry and adaptive physician profiling and constant automated discussion board monitoring, enabled by interconnectivity and automation of the DQS, networked members of the NPD can be placed into established "thought incubators". These small expert groups of physicians, compiled from pools of varied subspecialties, can participate in developing blueprints for novel therapeutics. These incubators can be formed at the behest of external clients or from any single networked physician. If generated from internal sources (either from the NPD or through automation from the DQS), the highly valued resulting end-products from these incubators can be sold to external agents for further development. This provides yet another avenue for corporate profitability based upon the unique construction and knowledge-ownership of the business platform.

Finally, all the physicians within the NPD would provide a large network of sophisticated, well trained "eyes" to carefully monitor the pharmaceutical industry and scientific literature for emerging treatments or side effect profiles that may have significant financial consequences. Thus, the novel system and method can automatically poll member physicians for investment advice by maintaining and accessing member physician industry expertise profiles, and may automatically screen potential investments to physician members with appropriate expertise profiles. The system and method can automatically route the collected observations and insights of member physicians to the managers of the IIV, further enhancing the unique advantage of this business platform. At the center of this advantage and what separates it from other previously established networks, is the equity-vested and interconnected interests of all the participating members.

Taking advantage of the rapidly evolving biotechnology market requires fluid dissemination of information as well as instantaneous feedback from end-users; in this case, physicians. Enabling communication and access to a virtual conferencing landscape composed of these physicians, via handheld or other mobile wireless devices will allow the IIV to take full and unique advantage of its invested end-user database.

The IIV may also include specific software and hardware devices that allows tracking of physician investments and their relative daily change in value, distribution of shares and dividends, portal for mutual interaction between DQS and the IIV in order to extract the maximal value from the intellectual commodity of the NPD. The latter may again be facilitated by the enablement of instantaneous communication devices.

In one embodiment, the present invention distributes first and second requests for physician intellectual work product respectively to first and second sets of physician members. In this embodiment, the invention also stores and/or transmits first physician intellectual work product generated by the first set of physician members in response to the first request for physician work product and stores and/or transmits second physician intellectual work product generated by the second set of physician members in response to the second request for physician work product. This embodiment of the invention may also receive first and second payments corresponding respectively to the first and second physician intellectual work products and may invest the first payment in accordance with advice received from a third set of physician members and may invest the second payment in accordance with advice received from a fourth set of physician members, and wherein ownership of the combined invested first and second payments may be held by a fifth set of physician members. In one embodiment the fifth set of physician members includes all of the physician members. In another embodiment, all of the first, second, third, fourth and fifth sets of physician members differ from each other. In still another embodiment, at least two of the first, second, third, fourth and fifth sets of physician include the same members.

The present invention also includes a computer system for managing consultation requests comprising: (1) at least one processor; (2) a first storage in communication with the at least one processor, wherein first and second rating values are stored in the first storage; (3) a first communication port in communication with the at least one processor, wherein the first communication port is configured to receive first data representing a consultation request, and wherein first software instructions are executed by the at least one processor to process the first data and to send second data representing the consultation request to first and second reviewers; (4) a second communication port in communication with the at least one processor, wherein the second communication port is configured to receive third data representing a response to the consultation request provided by the first reviewer and is also configured to receive fourth data representing a response to the consultation request provided by the second reviewer, and wherein second software instructions are executed by the at least one processor to process the third and fourth data and to send to a requester fifth data representing the responses to the consultation request provided by the first and second reviewers; and (5) a third communication port in communication with the at least one processor, wherein the third communication port is configured to receive sixth data representing a payment value corresponding to the value of the responses represented by the fifth data, wherein third software instructions are executed by the at least one processor to process the sixth data, to combine a value represented by the sixth data with seventh data representing the value of an account of which each of the first and second reviewers owns a fractional share to calculate a modified account value, to calculate a modified fractional share of the account owned by the first reviewer based on the first rating value, and to calculate a modified fractional share of the account owned by the second reviewer based on the second rating value. In certain embodiments the first, second and third communication ports are the same communication port.

In still another embodiment, the invention includes a method for processing consultation requests comprising the steps of: (1) sending a first consultation request to first and second experts; (2) receiving first answers in response to the first consultation request from the first and second experts; (3) analyzing at least one of the first answers to provide a first rating associated with the first expert; and (4) calculating a first fractional ownership in an asset based on the first rating, the first fractional ownership owned by the first expert. That embodiment may advantageously also include the further steps of: (5) analyzing at least one of the first answers to provide a second rating associated with the second expert; and (6) calculating a second fractional ownership in the asset based on the second rating, the second fractional ownership owned by the second expert. The embodiment still further advantageously includes the further steps of (7) sending the first answers to a customer; and (8) receiving a payment, wherein the value of the asset is based, at least in part, on a value of the payment. In another embodiment, the invention comprises computer media upon which are stored instructions for carrying out the foregoing steps.

BRIEF DESCRIPTION OF THE DRAWINGS

FIG. 10 illustrates a user interface in one embodiment of the present invention that a member may use to establish or maintain personal information.

FIG. 11 illustrates a user interface in one embodiment of the present invention that a customer may use to establish or maintain information.

FIG. 12 illustrates a user interface in one embodiment of the present invention that a customer may use to submit a question.

DETAILED DESCRIPTION OF THE PREFERRED EMBODIMENT

Figure 1:
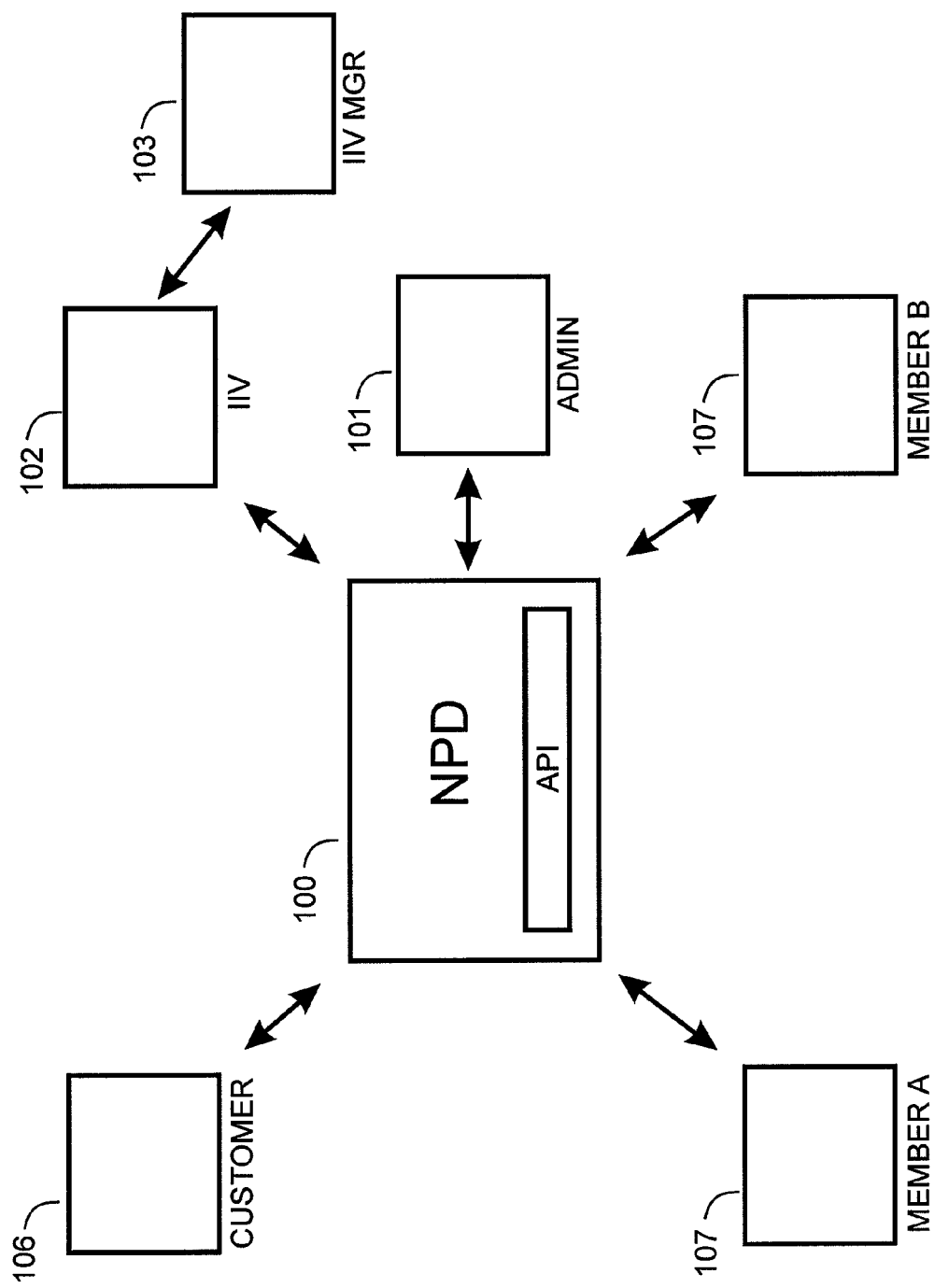
FIG. 1 illustrates an embodiment of the present invention including an NPD and IIV, customer interactions, member interactions, and administrative interactions.

Various inventions and embodiments of those inventions are disclosed. Aspects of multiple inventions may be represented in combination by single embodiments, while other embodiments may represent individual inventions. Combinations of embodiments may deliver advantages not inherent in the constituent embodiments.

Throughout these descriptions, certain embodiment-specific details such as hand-held, mobile or non-mobile devices, computers or components, fields of expertise, industries, types of professional, types of financial instruments, data types, algorithms, rules, and conventions will be referenced. This is done to illustrate particular embodiments, and not to limit the scope of any of the disclosed inventions. Thus, nothing in the drawings or this detailed description should be construed to imply that any exemplifying particularity of a discussed or illustrated embodiment is a requirement of any claim.

Figure 9:
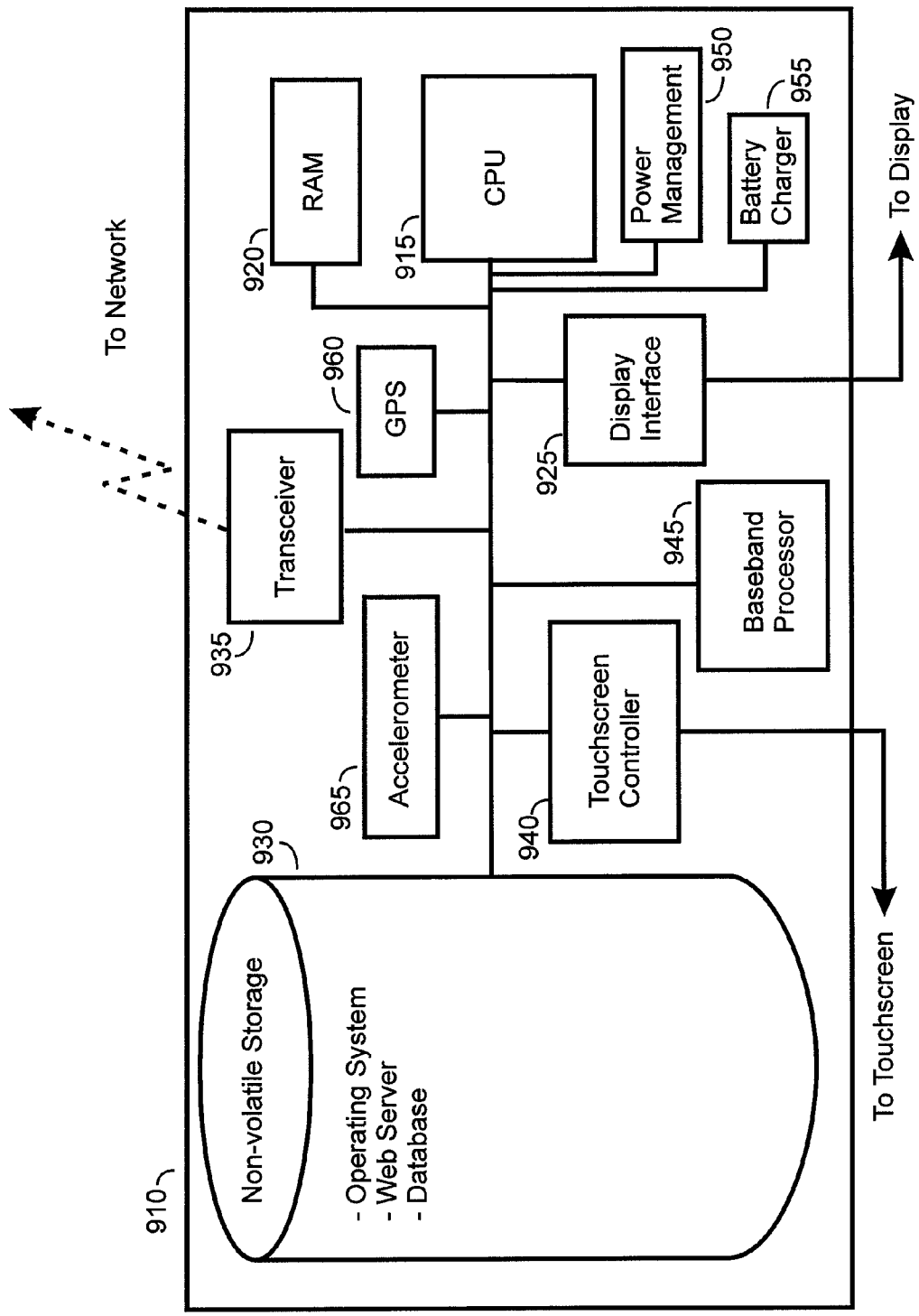
FIG. 9 illustrates components of a client device in one embodiment of the present invention.

Some of the embodiments refer to computing systems. More fully discussed in the descriptions of FIG. 9 and FIG. 10, a computing system may be one or more general purpose computers or processors or their functional equivalents, such as programmed FPGAs or virtualized hardware. Embodiments of server computing systems, as illustrated in FIG. 9, generally run operating systems in the Microsoft Windows™, Apple MacOS™, or UNIX™ families. Embodiments of client computing systems, as illustrated in FIG. 10, may run operating systems similar to those used by server computing systems as well as more specialized operating systems such as Windows CE™, Android™ or SymbianOS™ and even device specific operating systems such as those used on the iPod™, iPhone™, or BlackBerry™. One of skill in the art will appreciate that the evolution of hardware and software and the requirements of a specific embodiment may influence the computing systems used in any particular embodiment without departing from any invention. The various embodiments discussed herein may run on common or distinct computing platforms.

At a high-level, some embodiments enable expert members to rapidly access one another, to access and be accessed by one or more customers or community fund manager, and to access and be accessed by one or more administrators through interfaces including desktop computers, laptop computers, mobile handheld, and other wireless hardware devices.

For example, some embodiments of community infrastructure facilitate conferencing, consulting, document sharing, inter-disciplinary brain-storming, and other interactions among expert members. External customers can submit consultation requests or survey questions to the community, paying for the access either with currency or with royalty rights or fungible interests such as shares or options. In addition to retaining profile information about member experts, some embodiments of the community infrastructure also allow or require an evaluation of the responses experts provide. In some embodiments, the quality and quantity of an expert's participation in the community, including their engagement in the interactive aspects of the community and the nature, quality, and quantity of their profile information and publications, are also evaluated. Any evaluations, recorded behavior, or profile information is used by some embodiments to provide sophisticated statistical analyses of the responses to questions or surveys submitted by customers or by community fund managers.

Embodiments may address compensation of experts in different ways. For example, a portion of any payment may be directly remitted to a responding expert while a portion may be divided among all of the experts in correspondence to their participation in and value to the community, assessed using criteria similar or identical to those used in analyzing the responses to questions. Payments not immediately disbursed may be pooled in a community investment fund. In some embodiments a community investment fund focuses on investments that are pertinent to the expertise of the community (for example, the community fund associated with a community of doctors may invest exclusive in biotechnology and pharmaceutical companies). In some embodiments, the community investment fund is transformed into a value-added investment fund because some investment decisions are made based at least in part on the expertise of the community.

Using the novel systems and methods disclosed herein, an expert community can convert the expertise of its members into fungible assets in several ways, including: adding value to a community investment fund, marketing the expertise of the community, spinning off or licensing innovations developed by community members within the community, and allowing third party investors to join the community investment fund. Experts are encouraged to submit quality responses and to otherwise participate in the community because, for example, they are compensated at least in part on how other members or customers value their contributions or by the value their contributions add to any community investment fund. In some embodiments, the various revenue generating mechanisms and the way in which they feed back into the compensation of individual expert members also help encourage high quality contributions, foster involvement in the community, and attract high quality members. The rating and evaluation mechanisms, along with the ability of community administrators to direct quality-control questions to the membership in a way that is essentially indistinguishable from customer or member originated questions, are also ways in which some embodiments can maintain the quality of the expert responses.

System Overview

FIG. 1 provides a high-level overview of an embodiment of the present invention. It will be understood that, while described in the context of an expert community of physicians, the invention is not limited to the medical community, but rather its mechanisms and advantages apply to any other field where knowledge and intellectual work product have value. Referring to FIG. 1, a Networked Physician Database (NPD) 100 facilitates the establishment of a community of experts, the creation of a collective intelligence representing the aggregate expertise of the community, communication among members of an expert community (EC), surveying of members of that community, and any compensation of the members of that community. The NPD 100 may include one or more computer-based systems which may communicate with each other, preferably via a high performance network or connectivity protocol.

Connected to the NPD 100 is an Internal Investment Vehicle (IIV) 102. The IIV 102 may include one or more computer-based systems, and may include the same computer-based system as the NPD 100. The IIV 102 supports the management of one or more community investments (CI). One or more IIV managers 103 can connect to the IIV 102 locally or via IIV clients for IIV administrative purposes or for IIV management purposes, including forming and implementing an investment plan and carrying out investment transactions. An investment plan of the IIV 102 may be based in part on information provided by members of the EC, either directly or through the NPD 100. The IIV 102 or its managers may combine this expert information with other information such as that from external information sources and may engage in transactions with various entities in financial markets to manage the CI. Additional descriptions of illustrative examples of the IIV are provided in FIG. 3.

Also shown in FIG. 1 is a customer 106. In one embodiment, the customer 106 may interact with the NPD 100 to register, to submit questions, and to receive and analyze responses to those questions. The customer 106 may, in one embodiment, interact with the IIV 102, such as, for example, to provide the IIV 102 with currency or other consideration as part of its payment for access to the NPD 100. Other connectivity configurations are possible, depending on the particular deployment configuration of the IIV 102 and NPD 100 in a given embodiment. For example, the customer 106 may provide payment to the NPD 100, which may then pass it, possibly after accounting or processing, to the IIV 102.

Experts 107 may also interact with the NPD 100. As discussed below, they may do so through a variety of client systems, including handheld devices, laptop or desktop computing systems, including any device supporting a web browser with appropriate connectivity. Typical interactions with the NPD 100 will be to register as a member of the community and to update registration and demographic information, to submit questions to members of the expert community, to receive and respond to surveys and questions, and to otherwise interact with other community members and evaluate the contributions and interactions of other community members. Experts 107 may also interact with NPD 100 or, in some embodiments the IIV 102, to establish a payment or compensation protocol, to view account or investment information and to confirm payment receipt and/or payment processing specified by the expert 107.

As mentioned, to the extent that various named components are further composed of subcomponents including multiple computing systems, such computing systems are preferably connected by high performance protocols such as high speed local area networks or rack interconnect protocols. Other means of connectivity, such as that provided by cloud computing infrastructures or other distributed computing protocol, can also be used, and it will be appreciated that the present invention is not limited by particular connectivity strategies, components or protocols. If not using the same computer platform, the IIV 102 and NPD 100 are preferably connected over a high speed WAN. Some embodiments may use other protocols.

In FIG. 1, client platforms, or clients, including those associated with customers 106, members 107, administrators 101, and any IIV managers 103, connect to the NPD 100 or the IIV 102 from computing systems which are distinct from the computing systems that are included in the NPD 100 or IIV 102. These clients may connect to the NPD 100 or IIV 102 via any of a variety of network and connectivity protocols, including private networks, virtual private networks, secure internet connections, and standard internet connections. The performance profile of the connectivity mechanism may impact the user experience such that the better the connectivity the better the experience of interacting with the NPD 100 or IIV 102.

The NPD

This section discloses information about embodiments of the NPD 100, and additional information about the NPD 100 and its components may be found in other sections.

Figure 2:
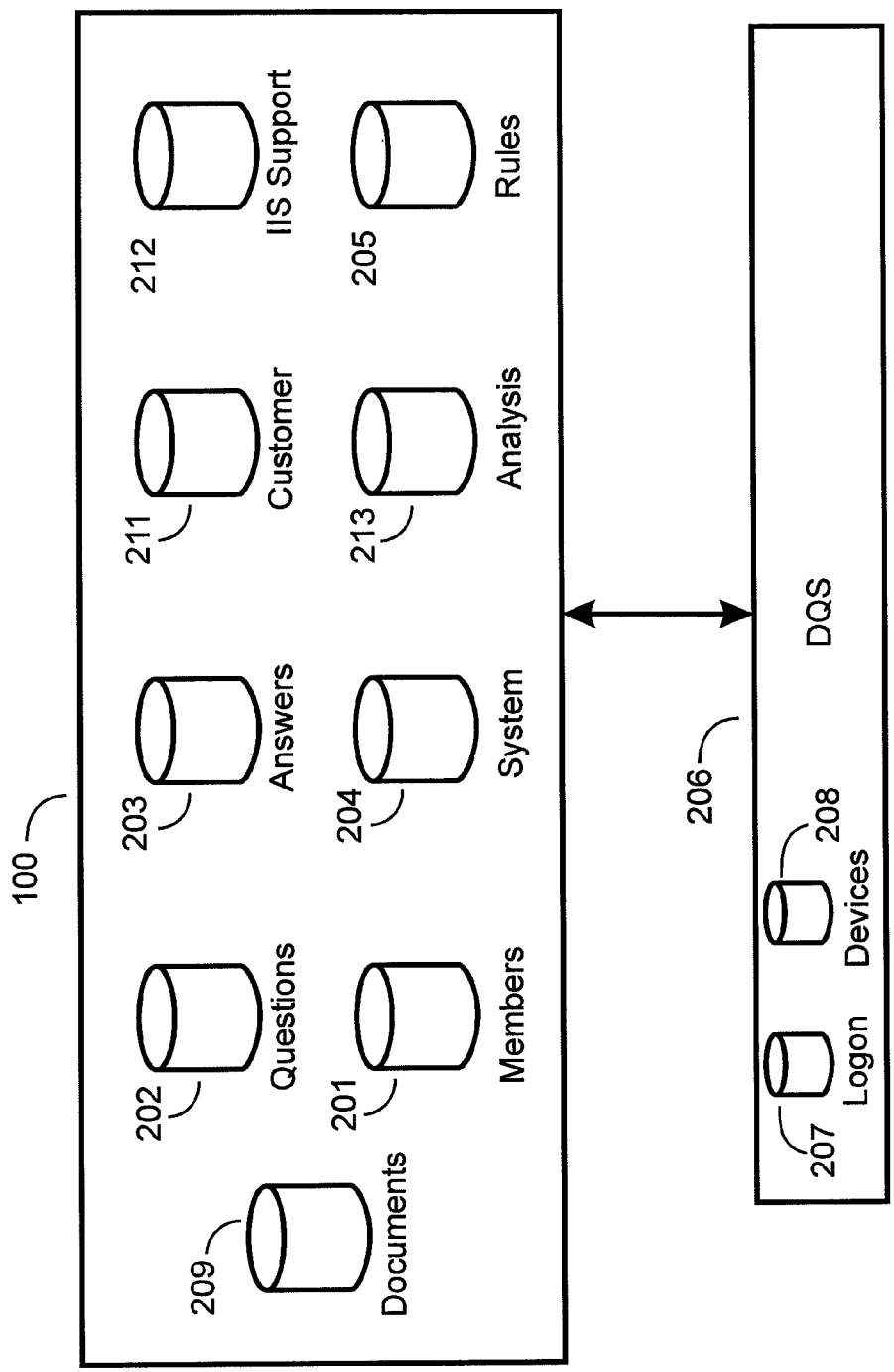
FIG. 2 illustrates components of an NPD in one embodiment of the present invention.

FIG. 2 illustrates an embodiment of the NPD 100. As illustrated, the NPD 100 may provide for maintaining information about expert members 107, for facilitating the entry and storage of questions for those members 107, for soliciting answers from members 107, for processing those answers for presentation to the questioners, for evaluating the answers, and for using those evaluations in determining any compensation allocated or remitted to expert members 107. Some embodiments of an NPD 100 may perform only a subset of these functions, and some embodiments may perform additional functions.

As described further below, the NPD 100 may compensate or benefit members in accordance with their contributed expertise by tracking for each member a fractional shares of one or more community investments (CI), preferably one that realizes its success by itself leveraging the expertise of the community. The NPD 100 may employ security components that protect the computing systems, the software running on those systems, and the communication among the components and with client computing systems (member, customer, and manager). Examples of such security components are firewall, VPN, encryption, and intrusion detection systems.

In one embodiment, the NPD 100 may include a member database 201, a question database 202, an answer database 203, a survey database, a system datastore 204, a customer database 211, an IIV support database 212, an analysis datastore 213, and a business rules engine 205. Some embodiments include a documents database 209 as well. In one embodiment, access to the NPD 100 is controlled and protected by a data query system (DQS) 206 which may maintain its own utility datastores such as a logon database 207 and a store of registered devices 208. While all of these components may run on the same server computing system, one or more of them may reside on other computing systems and each may also be distributed across one or more computing systems. Also, other embodiments may factor the data stored in the NPD 100 differently such that there are more or fewer datastores with the data organized along different lines. Implementation options include consolidating the various databases and datastores in a single relational database or distributing them over various flat file and object oriented datastores. Different datasets may be consolidated or organized differently in some embodiments. For example, some embodiments may store the logon and registered device information in the system datastore 204. Similarly, other embodiments may not have a business rules engine 205 and instead rely on data integrity rules or client-side logic to enforce the business logic of the NPD 100, and some embodiments may allow direct access to the various subcomponents without the mediation of the DQS 206.

In addition to what is described in the paragraphs immediately following, examples of database structures in particular embodiments are presented further below. The member database 201 may contain demographic and subject matter information about member experts. For example, if the embodiment is supporting a community of medical experts such as doctors, then the member database might have each member's name, contact details, practice locations, formal education, honors and/or awards, publications, specialty information, and/or affiliations. In this embodiment, the member database 201 also contains a cumulative rating of each expert, based at least in part on the ratings assigned to that expert's answers. In other embodiments that cumulative rating might be determined dynamically, when needed, or there may be no such rating at all. The member database 201 may be configured to include or integrate with a document management system, which may include the document database 209. The document management system contains or refers to a member's information library including their manuscripts and articles. Items within the information library can be made available for other members to view and, in some embodiments, to peer review. The document management system or, in some embodiments, a dedicated social networking component allows for discussion boards and forums open to members of the community. Thus, in the example of a configuration configured for medical experts, an NPD 100 may store work product and index it automatically by one or more identifying criteria such as, for example, completing physician, client, survey, date, title, study, product and/or related subject matter.

The NPD 100, in some embodiments, may invite or place doctors into thought incubators based on their profiles, their responses to questions, or their involvement in social activities such as discussion boards. Thought incubators are relatively small expert groups, compiled from pools of varied subspecialties, who can engage in advanced conversation about, for example, novel therapeutics. In some embodiments these incubators can be formed at the behest of external clients or from any single networked physician. If the ideas are member generated, the highly valued resulting end-products from these incubators can be sold to external agents, including customers, for further development or they can be otherwise monetized.

Similar to the member database 201 are the customer database 211 and the CIS support database 212. Respectively, these contain information about other entities that may submit questions to community members: customers and IIV managers. For each customer, in addition to basic identifying and contact information, the customer database 211 will have information about the customer's billing and payment plans and about any restrictions on the members to be solicited for feedback to the customer's questions. The customer database also contains a list of logon credentials associated with that customer. This mechanism allows customers to provision their own internal users to access the NPD 100. Different access privileges and billing information may be associated with each such customer user. In some embodiments, users may begin the registration process independent of a particular customer and then declare an association with a customer, which will be established once that customer accepts the association.

Information may be stored in a redundant fashion. For example, as just described, billing information may be stored or associated with both a customer's entry in the customer database 211 and the customer's questions in the question database 202. As shall be described, it may also be stored in the analysis database 213. In one embodiment, this may be overlapping if not actually redundant because sophisticated billing and contract structure may incorporate information about the questions asked, the answers received, and particular information about the customer itself. In some embodiments, such information may be associated with fewer entities or may not be stored at all and instead calculated based on business rules and the necessary underlying data. This type of flexibility in where data associated with multiple entities is stored or if it is derived when needed is inherent in the implementation technology.

The IIV support database 212 contains information about the IIV managers 103. In one embodiment it allows questions in the question database 202 to be associated, through the IIV support database 212, with identified entities. It is also used, for example, to allow IIV managers 103 to access other NPD 100 features. In some embodiments it may also store the valuation and apportionment information used to determine the value of each member's stake in the community investments (CI) managed by the IIV 102. In other embodiments some of this information may be managed and maintained by the IIV 102 or an affiliated third party, and stored in the NPD 100, for example, for performance and convenience reasons.

In addition to the information mentioned above, databases containing information about members or users of the NPD 100 may also contain information to identify any client computing devices that the member or user chooses to register with the NPD 100. Embodiments supporting device registration may allow such devices to access the NPD 100 without an explicit user logon or may allow caching of data on the client device, for example. Other embodiments may provide these features without requiring device registration and some embodiments may deliver additional benefits in exchange for registration or not allow any unregistered client computing systems to access the NPD 100. Registration may be keyed to a unique device identifier that the device or device operating system provides or may be keyed to a data value that is established by the embodiment and stored on the registered client computing system.

Some embodiments may organize information about members, customers and customer users, IIV users, and system managers in different ways. For example, a single user database might consolidate information about all such users, and data fields associated with an individual might indicate the user's type and institutional affiliations.

The question database 202 contains questions as submitted to the NPD 100 and metadata associated with those questions. As used herein, a question may be any form of consultation request that solicits feedback from an expert member. Examples of question metadata include the date and time the question was entered into the system, a link back to the submitter (typically a member expert, a customer, an IIV manager, or an administrator), links to any answers, and links to any analysis of answers to that question. Other data includes references to the cost, cost structure, and payment mechanism associated with the question. Also associated with a question is information indicating when and how often answers to the question should be solicited, what subset (if any) of the member community should be solicited, and whether or not the source of the question or the identity of any responding expert should be revealed.

Answers to questions are stored in the answer database 203. In one embodiment, answers are associated with a question in the question database 202 and with a particular run, distribution, or solicitation of answers to that question. Each answer is also associated with the member who was the source of that information. In some embodiments, each answer is also associated with any ratings of that answer. Each rating consists of the rating itself and may also include a reference to the source of the rating and a reference to explanatory or supplemental information contributed by the rater. In some embodiments, ratings are associated with anonymity flags that indicate, for example, whether the identity of the rater should be available to the person being rated or to the entity that submitted the question.

Some embodiments may also support a survey database, which may reside in the questions database 202. A survey is a collection of related questions. Although any questions may be part of a survey, typically each survey question requires a short answer or an answer from a limited set of options (such as a degree of 1-5, true/false, or multiple choice). The questions in a survey may be related in a variety of ways, such as by subject matter, by target audience, or by origin. The questions in a survey may be grouped together for statistical purposes or otherwise not share any apparent commonality. It will be understood that in this disclosure the terms "question", "query", and "consultation request" are often used interchangeably. Although this section distinguishes between a survey and a question, it will be understood that other sections may not. An example of a question is "Please describe the treatment protocol for a patient exhibiting the following symptoms . . . ". Questions included on or eligible for a survey might range from the more mundane "How many people live in your household?" to the more topical "If an alternative medicine treatment with peer reviewed efficacy but no AMA or FDA approval were available to a patient who could not afford pharmaceutical relief, would you prescribe the alternative treatment?"

In some embodiments, questioners may choose to directly submit surveys for distribution to the expert community. In other embodiments, they may indicate that a question can, at the discretion of the NPD 100, be included in a survey. The NPD 100 may automatically batch questions into surveys based on business rules, an analysis of the subject matter of the questions, an analysis of the distribution list for the questions, or other indicia that a survey would be appropriate.

Also, entire surveys or questions on surveys (as well as individual questions) may be sent to experts by the NPD 100 either automatically or at the discretion of administrators. By gauging the responses to these questions or surveys, the NPD 100 has an additional way of monitoring the involvement of expert members and the quality of the contributions. In addition to being evaluated similarly to any other response, responses to NPD 100 originated questions and surveys may also be compared to responses to previous runs of the same question, which may indicate whether community members have kept pace with developments in the field or are arbitrarily responding to questions without support for their responses, for example.

In one embodiment, the NPD 100 may also include an analysis database 213. The analyses stored in the analysis database 213 are each associated the analyzed answers and are thereby associated with the question being answered. An analysis may be associated with access control information to indicate whether it is viewable to entities other than the source of those questions and, if so, what information may be available to those entities. The access control information may indicate, for example, whether or not viewers can update the analysis with commentary (which is also maintained in the analysis database 213), can manipulate analysis variables, or can have access to different types of analyses. In other embodiments, this information may be stored elsewhere, such as in the question database 202, or may be linked to or derived from other properties associated with the source of the question, the question, and the answers. An analysis may also have associated billing information. In some embodiments it is possible that a single analysis will be built from answers to more than one question. When those questions are associated with different entities or would otherwise be subject to conflicting billing and access rules, embodiments can resolve this in a variety of ways. Some embodiments may not allow such analyses or may require a new entity be established to accommodate the billing and access rules to be applied. Some embodiments may act in accordance with instructions from the entities and apply the billing and permission according to the procedures they approve. Some embodiments may require that all of the properties associated with one and only one of the entities apply and leave it to the entities to resolve any administrative and billing issues. Embodiments may take advantage of the association between each logged on user and one or more entities in the member database 201, customer database 211, and IIV support database 212 to determine how a particular user's access of an analysis should be handled.

One embodiment of an NPD 100 includes a DQS 206. This DQS 206 is an abstraction layer that presents an API or interface that hides the implementation details and lower level access protocols associated with the various subcomponents of the NPD 100. Typically, a DQS 206 is implemented using an application server or a similarly configured server computing system capable of presenting HTML, AJAX, and/or device specific interfaces to client computing systems and also capable of presenting an API to which device specific client user applications (e.g., Mac, Windows, Linux, Blackberry, or iPhone) can be written. Some embodiments include a DQS 206 with less functionality, and, as mentioned, some embodiments may forego a DQS 206 completely.

Other components that may be included in the NPD 100 include the system database 204 and the business rules engine 205. The system database 204 contains information about the state of the NPD, including error information, component availability, and performance information. The system database 204 also contains information about what clients are currently logged on and what client computing systems or devices are currently interacting with the NPD 100.

In this embodiment, the business rules engine 205 contains logic and executable code for coordinating the behavior of the various other components of the NPD 100. In some embodiments, the functionality of the business rules engine 205 can be implemented using stored procedures and other executable mechanisms provided by the previously described components or by a stand alone integration engine or NPD system software component. In some embodiments, the functionality is provided by the DQS 206, which will ensure that the business logic is maintained when it responds to client requests and pushes information out to clients.

The business rules engine 205 is largely responsible for ensuring that the components of the NPD 100 remain in a consistent state, that the DQS 206 is provided with appropriate information to present to client devices, and that the client requests received through the DQS 206 are implemented with appropriate behavior by the NPD components. For example, the business rules engine 205 in the sample embodiment implements the solicitation of responses to a question as described below, in the detailed discussion of FIG. 4. In some embodiments the business rules engine 205 will invoke routines or procedures on other components of the NPD 100.

In some embodiments, the business rules engine 205 validates data and ensures that the NPD 100 does not allow any behavior that would be contrary to the permissioning and access rules previously described, or to business level requirements such as requiring members to complete registration before responding to or submitting questions requiring customers to have verified their payment capability before submitting questions. In some embodiments, the business rules engine 205 functions as described above, mapping high level tasks such as "solicit answers to a question" or "present a welcome screen" into executable steps, performing those steps or causing them to be performed, and marshalling any resulting information (if appropriate). In other embodiments, the logic associated with such tasks is represented by script programs (such as PERL scripts) embedded in web pages served to clients by the NPD 100.

One example of a rule in the business rules engine 205 is one that may govern the circumstance when a member, for example a doctor, has indicated that she is now affiliated with an organization, such a pharmaceutical company. In one embodiment, the business rules engine 205 has a rule that requires that such a change be validated by the pharmaceutical company, if that company is registered with the NPD 100. Some embodiments may also have a rule that requires particular behavior to be taken if the company is affiliated with the IIV 102. The business rules engine 205 looks for the company in the customer database 211 and, when it finds the entry, locates the user tagged as the primary or administrative contact. It then compares that user's preferences with the current status of the user as indicated in the system database 204. Depending on the result of that analysis, it packages up the necessary information (for example, a link to the member's profile, identifying information about the member, the user's email address, and the user's device profile and identifier) and directs the DQS 206 to send an email or other message to an offline user, to present the user with an action item upon their next logon, or to alert a currently online user of the need to take action. The DQS 206, based on the information and request from the business rules engine 205, proceeds to execute the request using the user interface and style appropriate for the client computing device.

The databases used by the various embodiments of the present invention, including those illustrated in FIG. 2, may be implemented by any computing system running software capable of supporting a queryable data repository, including computer storage sufficient to store the respective data, and including computer processing sufficient to update and query the repository in a timely fashion. In some embodiments, a database may include multiple distinct sub-databases. The various databases and datastores may be implemented using relational database systems. Examples include an Oracle database, an IBM DB2 database or the MySQL database. These database software systems can run on the server computing systems as previously described. The business rules engine 205 may be implemented by software modules associated with the databases, such as rules, triggers, or extensions to the underlying database system of a given embodiment. Other embodiments include systems that are independent of but in communication with the databases, such as rules engines or business automation engines from TIBCO, Oracle, or Microsoft. Any information or data necessary for the business rules engine 205 to operate may be stored in a database associated with the business rules engine 205, or in one or more of the previously discussed database components.

In some embodiments, the NPD 100 provides portal or social networking functionality to members.

The IIV

This section discloses information about the IIV 102, and additional information about the IIV 102 and its components may be found in other sections.

Figure 3:
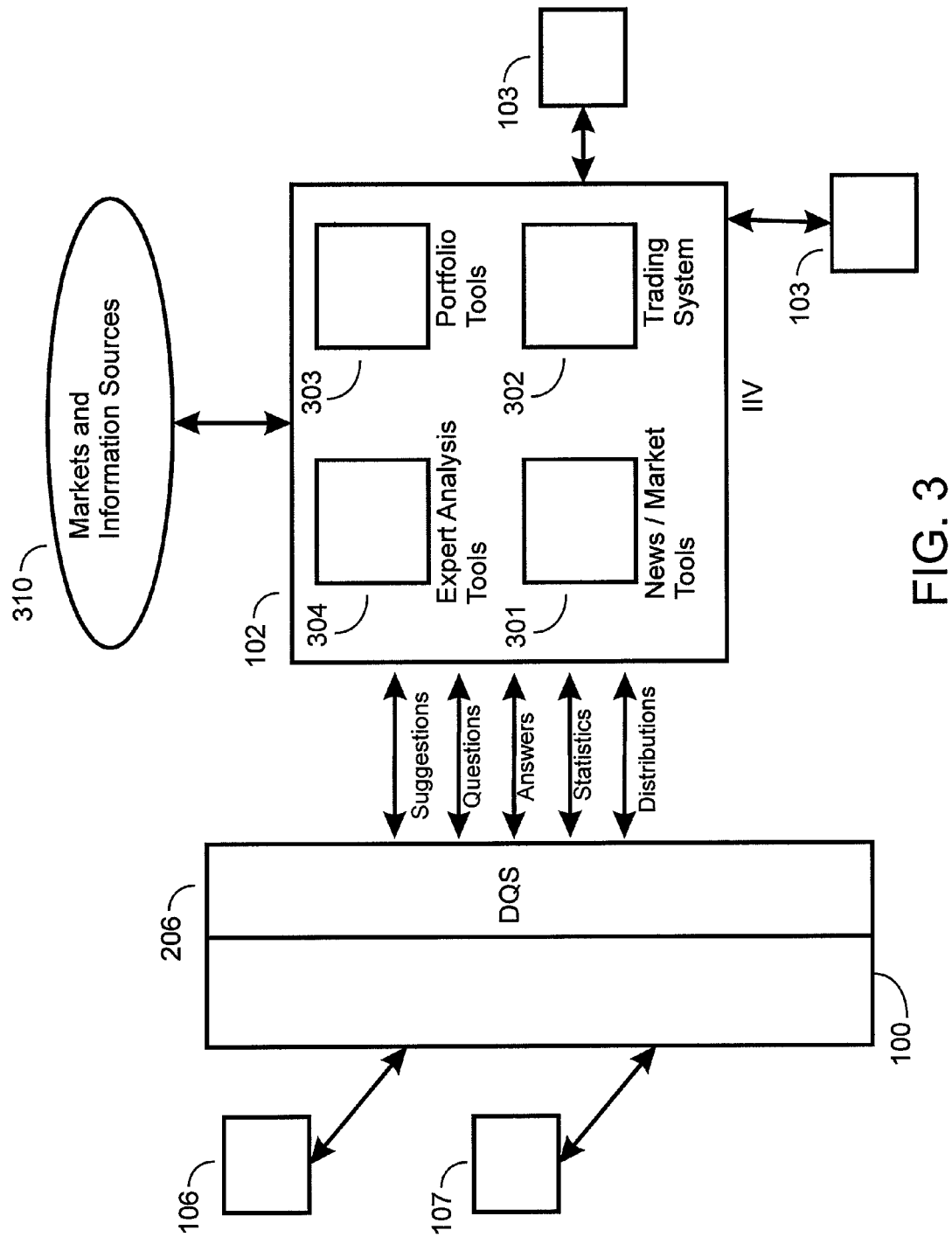
FIG. 3 illustrates components of an IIV in one embodiment of the present invention.

FIG. 3 illustrates an exemplary embodiment of an IIV 102. The IIV 102 provides functionality and includes components typical of a system for managing financial instruments and portfolios, as well as integration with the NPD 100 and its component systems. For example, the IIV 102 has connectivity to external sources of market news and information 310, including reports from technical sources, brokerages, dealers and financial markets. It includes news and market tools 301 for displaying and analyzing news, market data, and information (which may include web browsers, electronic journal subscriptions, and/or financial reports and studies such as those provided by E*Trade), trading system tools 302 for conducting transactions such as buying, selling, or otherwise modifying positions in any type of marketable securities that can be traded electronically (such as the tools provided by E*Trade), and also portfolio tools 303 to review current financial positions and portfolios (such as tools provided by Quicken). As used herein, "tools" means collections of software instructions that can be executed by a computer processor to transform particular types of input data into alternative representations for examination, analysis, visualization and/or comparison purposes or to conduct electronic tasks such as searches or transactions.

The IIV 102 may also include an Expert Group Intelligence Research and Analysis component 304 (ERA). In one embodiment, the ERA 304 comprises one or more tools which run on the IIV 102 server computing system. The ERA 304 interfaces with the NPD 100, preferably through a DQS 206.

Through the ERA 304, questions such as those about the viability of particular financial instruments or about market trends can be routed to one or more expert members of the NPD 100, much like any other question as described above. Typically, there is a correlation between the portfolio and financial instruments of the IIV 102 and the area of expertise of the community members of the NPD 100. If the expert members of the NPD 100 are generally physicians and other medical experts, then the associated IIV 102 would typically be used to manage community investments (CI) related to the medical device, pharmaceutical, and perhaps biotechnology or healthcare markets, and perhaps other markets familiar to and understood by physicians.

For example, if the IIV managers 103 become aware of an opportunity to invest in the stock of a particular pharmaceutical company they might submit questions and/or suggestions to the expert community about the particular pharmaceutical company, its product or prospects, about the health care system of the country where the country is located, or about the trends in the company's particular field. Other examples of questions an IIV 102 may submit are: "What do your patients indicate is the biggest obstacle to completing a rehabilitation regiment?" or "How is [company X] failing to meet your needs?"

In some embodiments, the ERA 304 performs some functions without ongoing interaction by the IIV manager 103. For example, an embodiment may automatically send a question seeking to explain a dramatic market movement, seeking feedback on FDA approvals of drugs or devices, or asking about the prospects of companies with pending IPOs. In some embodiments, the ERA 304 may present an interactive interface to the client computing devices used by an IIV manager 103. This interactive user interface, much like the interface presented by the DQS 206 in one embodiment of the NPD 100, may be tailored to the client computing device and may allow the IIV manager 103 to create, schedule, and target questions. In some embodiments, the interactive user interface is implemented via a series of web pages, which may include hyperlinks, mouse-over or hover-based content, pull-down menus or other controls, and which may be served to client devices by the NPD 100.

In some embodiments, an IIV manager 103 may take advantage of the ability of the ERA 304 to integrate other financial and market data into the analysis of the answers from the NPD 100. As previously discussed, in some embodiments an IIV manager 103 is also able to access the NPD 100 directly through the DQS 206 and view the analytics provides by the NPD 100.

This illustrates how the IIV 102 and NPD 100 transform a raw financial commodity into a value-added investment vehicle by leveraging the expertise of the member of the NPD 100. IIV 102 embodiments including automatic processing of responses from the NPD 100 or allowing IIV managers 103 to have real-time and near-universal accessibility to both expert feedback and trading tools encourage investment performance that surpasses the performance of other funds or vehicles that lack such features.

The present invention, in its various embodiments, may advantageously accommodate professional, ethical, and legal regulations governing the behavior of experts and of traders. The NPD 100 may have business rules that, for example, prevented questions about a company from being routed to a member affiliated with that company and which prevented an answer mentioning a company being sent from a member affiliated with that company, at least if the source of the question being responded to was the IIV 102 or an IIV manager 103.

One or more community investments (CI) managed via the IIV 102 may be independently-managed, where the IIV managers 103 are not themselves members of the community of experts but are professional portfolio managers. The ability to access group expert intelligence, such as by using the NPD 100, may advantageously provide an IIV manager with expertise that can be applied to make the best CI management decisions possible, which, in one embodiment may be to maximize the growth of a CI. Thus, the expertise of individual community members not only earns capital through customer payments, but also may advantageously increase the value of CI by favorable influencing how the capital comprising the CI is invested.

A CI may be funded using a variety of means. In some embodiments, the members of the expert community may be required or allowed to purchase shares in the CI with cash. In some embodiments, the payments or other consideration provided by customers of the NPD 100 (or some portion thereof) may be used to fund the CI, with the resulting shares held by the NPD 100 on behalf of the members. Some embodiments allow outside investors who are not members of the expert community to purchase a fractional ownership of the CI.

In addition to any shares they may have bought directly, in some embodiments members of the NPD 100 receive fractional shares of the CI as compensation for their participation in the community and, in particular, for responding to questions. The shares distributed in this way may come from shares held by the NPD 100 which, for example, correspond to the shares obtained with customer fees. Or they may be allocated by the IIV 102 either automatically or at the behest of the IIV managers 103. Shares so issued may come from pools of unissued shares or may be newly issued.

Given the real-time aspect of the financial markets, the IIV managers 103 may advantageously gain access to the system using their portable client computing devices and have the benefit of using portfolio management tools and also the expertise represented by the NPD 100. Indeed, because the NPD 100 allows for real-time interaction with community members via email, chat services, and handheld or portable devices, some embodiments are configured with appropriate business rules in the business rules engine 205 and permissioning in the various components of the NPD 100 such that the IIV managers 103 can solicit feedback from community members with particularly high reputations or specialties or can be alerted when the answers match certain criteria (such as including answers from a critical number of community members or from members with high ratings or specific specialties) so that they can act promptly and profitably on the information.

Like the NPD 100, the IIV 102 preferably runs on one or more server computing systems which may interact with each other using high performance protocols.

In order to safeguard the integrity of and any proprietary rights in the externally generated queries, as well as to prevent any SEC violations, all queries may advantageously be analyzed via the DQS 206 in such a way that information and results of external queries may not be accessible to the IIV 102. Strict security measures may preferably prevent inappropriate access to confidential material by any internal or other external parties. Signed agreements from all physician members may also be obtained (e.g. scanned and stored in the member database) to comply with all SEC and FDA rules and regulations, as well as constraints imposed by basic best ethical practices regarding patient care.

Consultation Requests

Customers 106 may submit consultation requests to an embodiment of the NPD 100 in a variety of ways. Some embodiments allow for particularized consultation requests in which an expert or a small group of experts are explicitly identified by name. Some consultation requests may consist of a single question or a small group of related questions which call for an expository response. Other requests may be surveys-style questions or even complete surveys, typically calling for short answers or for answers from a limited universe of possibilities.

In some embodiments, a consultation request from a customer 106 is accompanied by payment in hard currency. In some embodiments, payment can be in the form of royalty rights, stocks, options, or other fungible financial instrument. In some embodiments a combination of payment devices can be used. In other embodiments, customer payment may be received upon delivery of responses to the customer 106.

While some embodiments might remit some or all of the payment to the experts responding to the consultation request, either based on a flat rate or in an amount proportional to payment and the number of experts responding, some embodiments may use alternative means of determining compensation. For example, some embodiments may deposit all or part of a payment for use by an associated IIV 102. Some embodiments may record a notional dollar value associated with responding members, and then determine payment by allocating an appropriate number of shares or fractional shares of a CI managed by the IIV 102. Different embodiments may use different means of calculating the price/share equivalent, such as basing it on the closing value of one or more community investments (CI) that day, or the previous day, or a mark to market at the time payment is tendered by the customer. Embodiments allowing non-currency payments from customers 106 may value such payments using a nominal value, an arbitrary value, or any applicable economic or pricing valuation model.

Some embodiments support alternative pricing and payment mechanisms for customers 106. For example, customers 106 may incur a payment obligation each time they submit a consultation request, each time a response is actually solicited from member experts, or when statistically useful results are viewed or made available. In some embodiments, customers may purchase a fixed number of questions, for example. Also, the amount of payment may vary. For example, in addition to supporting pricing options based on properties of the customer and the customer's relationship with the NPD 100, some embodiments may base the price charged to a customer at least in part on the complexity of the consultation request, the number of experts from whom responses are solicited, whether or not particular member experts are solicited, the number of responses received, and the quality or statistical value of the responses received. Some embodiments may assign points or values to these factors and charge customers based on the number of points they consume. In some embodiments, these factors are determined at least in part by leveraging the expertise of the community. For example, some embodiments may assess the complexity of a question based on the time that community members spend discussing it or developing a response, or from internally generated questions that specifically ask for an assessment of a question's complexity. Similarly, in some embodiments the quality of the responses may be based on actual evaluations by other members, on comparison to a control group or other checks of internal consistency, or on the evaluations of the members creating the responses.

Figure 4:
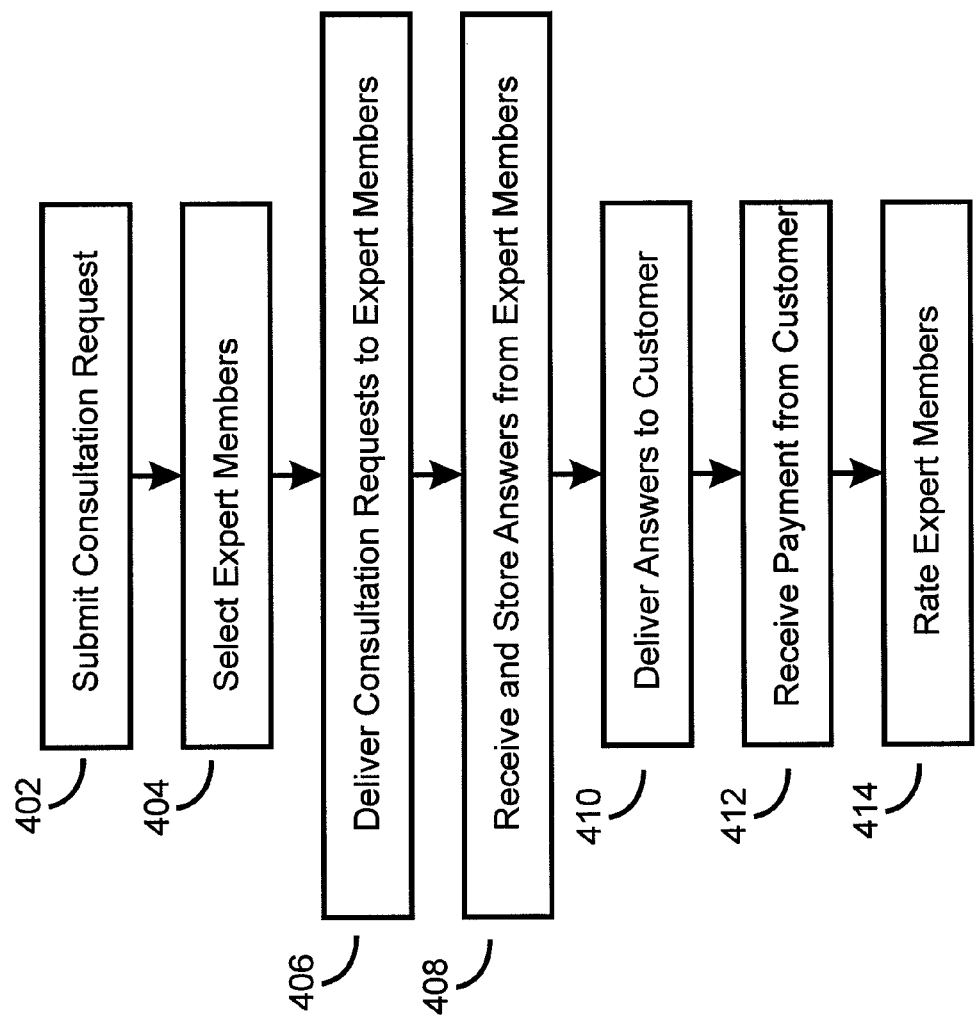
FIG. 4 illustrates steps performed in one embodiment of the present invention for processing a consultation request.

FIG. 4 illustrates at a high level the steps performed by one embodiment of the present invention to receive and distribute consultation requests among expert members and to process and deliver answers to a customer. In a first step 402, a customer 106 submits a consultation request to the NPD 100 whereupon it is stored in the questions database. In a second step 404, specific expert members are identified to respond to the consultation request. In a next step 406, the consultation request is delivered to each of the selected expert members. In a next step 408, the answers provided by each of the selected expert members are received by the NPD 100 and stored in the answers database along with the member ID of each respective responding expert member. In a further step 410, the answers are delivered from the NPD 100 to the customer 106, and in a next step 412 payment is received from the customer 106. In another step 414, each of the responding expert members is rated and a rating factor for each expert is generated or updated.

Soliciting Responses and Responding to Consultation Requests

Figure 5:
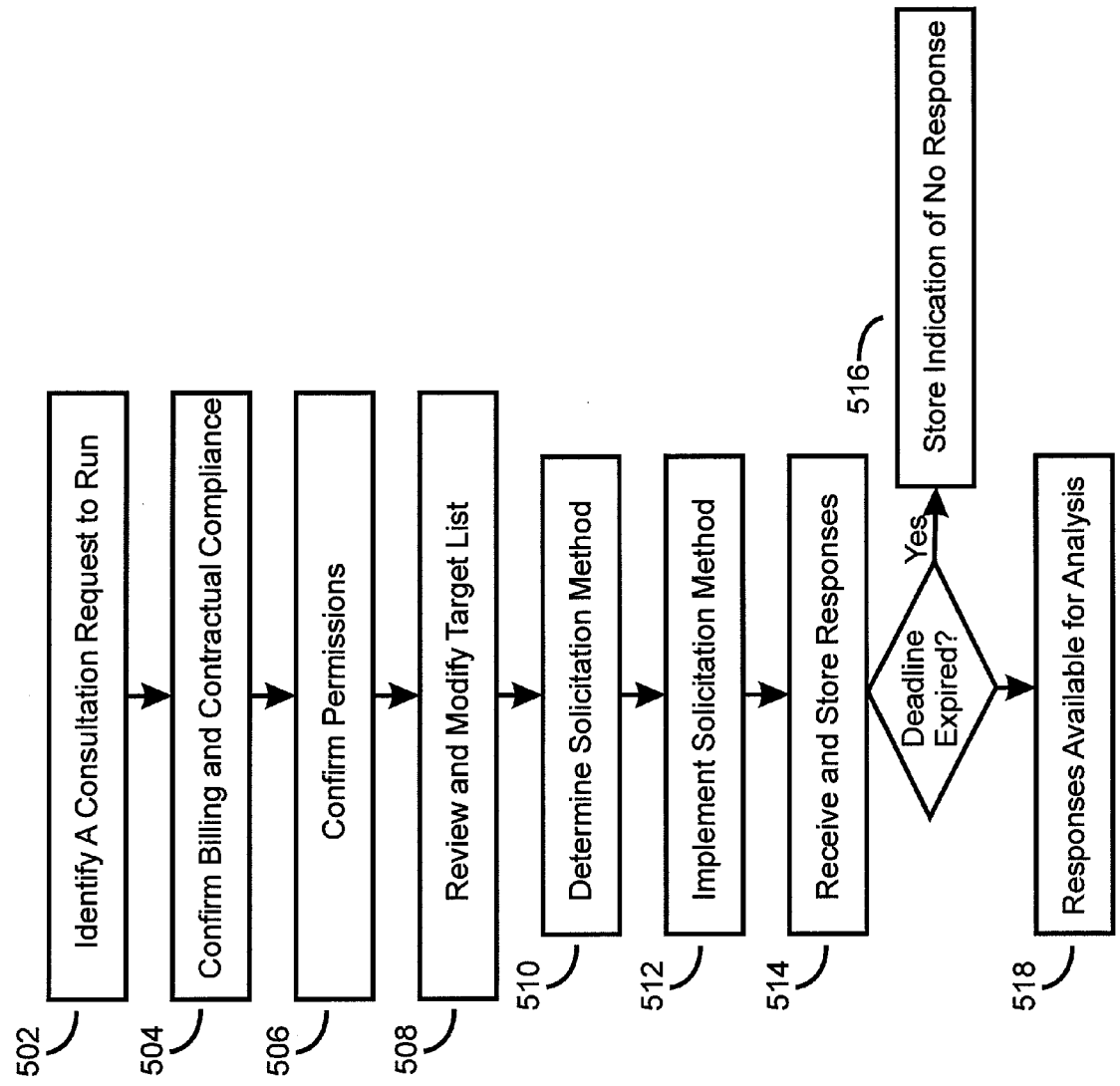
FIG. 5 illustrates steps performed in one embodiment of the present invention for the solicitation and receipt of responses to a consultation request.

The process by which an example embodiment of the NPD 100 solicits responses to a consultation request and the process by which those answers are received by the NPD 100 were introduced above. FIG. 5 illustrates in more detail steps that one embodiment of the present invention may perform as part of steps 404, 406, and 408 discussed in connection with FIG. 4 to solicit and receive responses to a submitted consultation request. In a first step 502, a business rules engine 205 identifies a consultation request to run. In a second step 504, the embodiment confirms that the entity submitting the consultation request is in compliance with any billing and contractual requirements. In a next step 506, the embodiment confirms that the submitting entity has the appropriate permissions for the consultation request to be run. In a next step 508, the list of targeted members from whom responses are to be solicited is reviewed and, if appropriate, modified. In a further step 510, the appropriate means or set of means for soliciting a response from each targeted expert member is determined and in a next step 512 the determined solicitation means are implemented. In another step 514, responses to the consultation request are received and stored. In a further step 516, records indicating any solicited member experts from whom responses were not received before the run timed out are stored. In a further step 518, the stored results of the run are made available for further analysis and presentation to appropriate users.

The illustrated embodiment may perform step 502 in a number of ways. For example, it may act in response to a request from a client to promptly answer a consultation request. This might happen if a member doctor needs an urgent second opinion or if an IIV manager 103 has identified a fast breaking financial opportunity. In some embodiments, the NPD 100 may regularly review the questions in the consultation request database 202 to determine if any are scheduled to run, or the question database 202 may proactively alert the business rules engine 206 of any scheduled solicitations.

Before proceeding, some embodiments may perform step 502 to ensure that various administrative and contractual constraints are satisfied, including contractual or billing requirements and perform step 504 to confirm that the entity submitting the consultation request is permitted to do so. Some embodiments or configurations of an embodiment may not solicit answers to the questions of an entity unless that entity has paid in advance. In such an embodiment, the NPD 100 might prompt the entity to pay as part of the solicitation process or take other appropriate action to alert the entity through specified contact information of its need to pay. Similarly, if soliciting answers would cause a user to exceed contractual or term of service limitations, then some embodiments may stop the solicitation process and inform the user of the situation. Some embodiments may allow the solicitation, depending on the nature of the limitation exceeded. Some implementations may allow otherwise extra-contractual solicitations if, for example, the solicitation is part of an ongoing field survey or is otherwise time sensitive. Some of these embodiments, as well as some embodiments that do not generally restrict the solicitation of responses as described herein, may restrict the questioner's access to the responses or the analysis of the responses until the problematic situation is resolved. Other examples of confirming that an entity is permitted to submit the consultation request for which responses are being solicited include confirming that the consultation request does not breach the anonymity constraints that might apply to the consultation request and confirming that the consultation request itself does not disclose information should not be shared, such as privileged patient data or insider commercial information. Some embodiments may perform this filter when the consultation request is submitted, but to account for changes in the filtering capabilities of the system between the time of submission and the time of solicitation, as well as to account for changing conditions, some embodiments may run or re-run the filtering at the time of solicitation.

The example embodiment of an NPD 100 performs step 508, building and reviewing the list of targeted members by starting with any submitted solicitation or target list. The solicitation list generally includes all members specifically identified in the consultation request, all members of subgroups identified, and all members who match any other search criteria specified. Some embodiments automate or partially automate selection of specific expert members through one or more selection criteria that are appropriate to the customer and the consultation request, including, for example, subject matter expertise, practice area, years of experience, age, gender, work schedule, positions held, courses taught, institutional and/or professional affiliations, training, education, publications, and prior opinions, among possibly many others. Also, some embodiments reduce or filter the solicitation list in a variety of ways. For example, contractual restrictions may not permit solicitation from more than a maximum number of members or from certain subsets of the membership (e.g., a client may have only subscribed to query podiatrists and have named a non-podiatrist in their query list). Similarly, some embodiments may filter out target members based on conflicts or other ethical or legal rules so that, for example, a consultation request about or from a company does not go to a board member of that company. Also, some embodiments may allow members to establish filters so that they only or preferably receive certain types of questions. Some of these embodiments will take that into account at this step.

Step 510 of determining the appropriate means or set of means for soliciting a response from each targeted member and step 512 of implementing those means may be performed by the business rules engine 205 and the DQS 206, using other data in the NPD 100. The method of solicitation may depend on the preferences of the solicited user, the preferences of the questioner, on whether or not the solicited user is logged in to the EIC 100, and on the client computing system the solicited user is using. For example, some embodiments may use one or more of emailing or messaging a member to prompt the member to logon to the NPD 100, emailing or messaging a member with the substance of a consultation request so that the member may respond, or alerting members upon logon that questions are awaiting their response.

When a response is received in step 514, the response is routed through the DQS 206 and ultimately stored in the answer database 203. The lack of a response by any given deadline may be similarly recorded as part of step 516. If an embodiment allows a member to change or modify a response then some embodiments will keep a change history for, among other uses, audit purposes. Some embodiments may also subject answers to filters (similar to the way some embodiments filter consultation requests) and, for example, remove or flag those answers that breach any anonymity constraints. In some embodiments, responses may be routed directly to the sender of the consultation request. Some embodiments may filter based on the requirements of the questioner, and some embodiments may not filter at all.

Once responses and non-responses are stored, the set of responses is made available in step 518. Any necessary and/or resulting data associated with the analysis is stored in the analysis database 213. In some embodiments responses may be made available as they are received, or based on criteria other than the passage of time or the receipt of a number of responses. Examples of appropriate criteria include a request from a client to prepare an analysis, the receipt of a specified number of answers, or the passing of a deadline. Some embodiments do not perform analysis, while others perform varying degrees. Analysis is more fully discussed below.

In some situations, for example if the consultation request is from an expert member and is styled more as a chat or conversation than as a survey, any analysis stage may be bypassed. This, in conjunction with other appropriate configurations, allows some embodiments to apply any other constraints (e.g., contract compliance and anonymity preservation) to all consultation requests and answers while allowing for near real-time communication when appropriate.

In one embodiment, a user may respond to a solicitation in several ways. Preferred embodiments will allow users to respond through the client interface, be it web based or device specific. Through the use of dedicated addressing or keywords in the body or subject of a message, some configurations allow members to respond via messaging or email. In some embodiments, interactive voice response systems may support telephonic responses.

Some embodiments will give users the option of answering all, part, or none of the consultation request, and some embodiments will also allow the member to further expand upon their response, such as by citing to other information in the NPD 100 or external to the NPD 100 or by explaining a response or declined response.

Ratings

Ratings or evaluations can have multiple roles. In some embodiments, ratings are used to determine the relative compensation of member experts. In some embodiments, ratings are a factor in the analysis of responses to a consultation request. Ratings may also be used, for example, in auditing procedures or in determining customer's bills.

Embodiments allow ratings to be assigned to a variety of information and user behavior. In some embodiments, responses to consultation requests can be rated, as can a consultation request itself. For example, a member expert's question on a community message board may be rated and the rating may be relatively high if the question is an insightful one or leads to a fruitful discussion. In some embodiments, even ratings themselves might be rated. Embodiments may also allow ratings to be assigned to assigned to, for example, articles or manuscripts that are published on or referenced by the NPD 100.

In one example, ratings may occur on at least two levels. Activities (e.g., responses to consultation requests) are rated and members themselves are rated. A member's ratings depend, at least in part, on the ratings of that member's answers. Some embodiments may not implement ratings, or may only implement one level of ratings.

Some embodiments enable different ratings for different contexts. In such an embodiment, one member may be able to review the ratings of other members relative to their expertise and promptness in responding to juvenile dosage levels while another entity, such as an IIV manager, may be able to review ratings corresponding to the financial contribution to the community. One implementation of such an embodiment involves the use of a rating-type table and a rating-record table. Each consultation request response submitted by a member is associated, through the records of the NPD 100, with that member, with the consultation request, and with the entity that submitted the consultation request. Moreover, any rating or evaluation of that response is similarly associated with the evaluator. In the example implementation, the rating-type table contains a record or entry for different categories. For example, there may be categories corresponding to expert specialties, such as an orthopedist-rating or a general-practitioner-rating. There may also be ratings associated with customers, such as Merck-rating, or with different topics such as a theory-rating or a patient-practice-rating. The rating-type table contains a list of these ratings, an identifier for each rating-type, and may also contain a link to a rating-rules table where the details of how to calculate the rating are stored. Finally, the rating-record table contains entries which each include a member's ID, a rating-type ID, and a value for that rating. In some implementation the value may be calculated by the NPD 100 when it is needed. Different rating types may be configured to attach a different relative weight to the ratings which they aggregate. For example, an IIV-rating may be based on all ratings of a member's activity, but give a higher weight to the ratings from IIV managers 103.

These different rating-types may be used, for example, to enable finer grained comparisons of member experts. An implementation of a compensation process may require that an amount be divided among a number of members according to their weighted ratings. If the members are being compensated in large part because of their expertise in neurology, an implementation might weight the members based in part on their neurology-rating and not, for example, on their general-practice rating. Similarly, if an NPD 100 is determining the target list for a consultation request, it may automatically attempt to include members who have received high ratings on their previous responses to questions from the source of the consultation request and on consultation requests in similar domains.

Some embodiments may allow entities other than member experts to submit ratings. For example, the IIV managers 103 might rate. Also, some embodiments allow customers 106 to rate. Some embodiments incentivize customer to rate or compensate them for taking the time to rate by, for example, directly reimbursing them for each rating submitted, discounting the bill according to the number or quality of the ratings, discounting future bills, enabling additional functionality for current or future interactions with the NPD 100, or promising a form of priority processing (such as, for example, attempting to give access to higher rated members or more rapidly making results available to the customer 106)).

Figure 6:
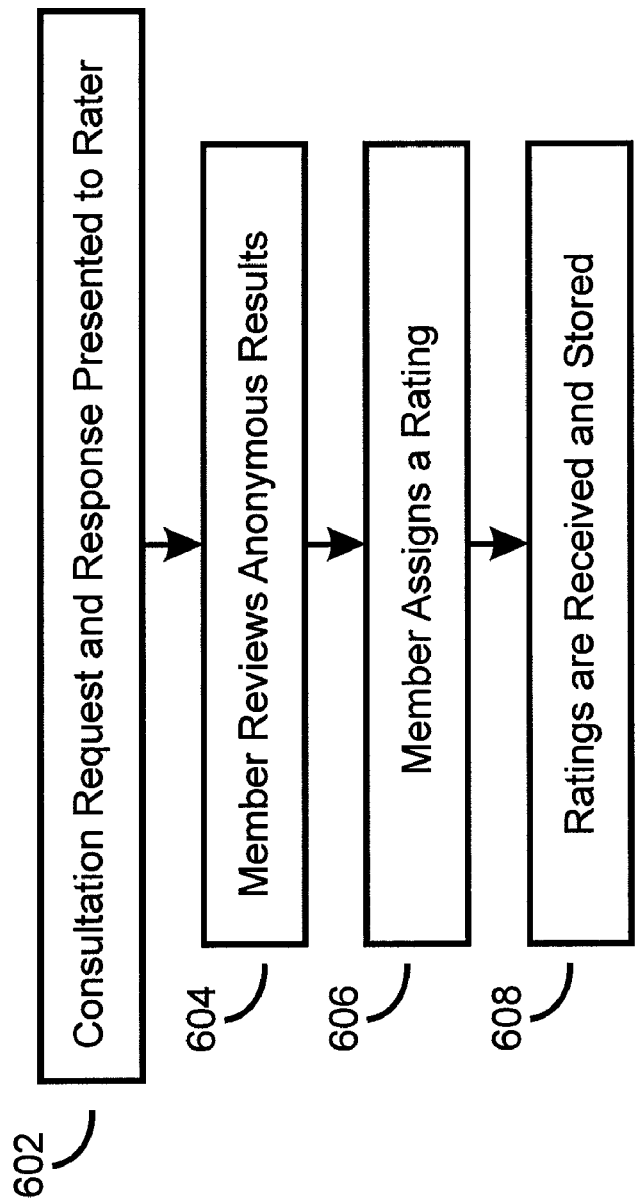
FIG. 6 illustrates steps performed in one embodiment of the present invention for rating or assessment of responses to consultation requests.

FIG. 6 lists steps involved in an illustrative rating process performed by one embodiment of the present invention. In a first step 602, a rater is presented with a consultation request and a response to that consultation request. In some embodiments, this consultation request may be one submitted by the rater and in some embodiments such a scenario is prohibited. In some embodiments, members will be assigned responses to review based, for example, on their expertise or ratings. In some embodiments, a rater can request to review additional responses, optionally in a particular subspecialty. In some embodiments, responses that are inherently non-anonymous can not be reviewed. Such responses may still be useful in the context in which they were asked, but some embodiments may flag them so that they can be treated appropriately: for example, excluded from certain analyses or contributing negatively to a member's rating if a non-anonymous response was not necessary or appropriate.

In a next step 604, the rater reviews the response, and in preferred embodiments, the rater remains anonymous. If the response was to a question sent by the rating member, then the NPD 100 may remove any identifying information from the response or not allow a questioner to review responses to her own questions. Preferred embodiments do not permit a rater to rate that member's own responses or activities. In some embodiments, the rating member will be prompted with ratings guidelines. This is particularly relevant to newer members, when any ratings guidelines change, or in embodiments with multiple types of ratings.

In a next step 606, the rater assigns a rating. The rating may, in some embodiments, also include an explanation of the rating or references to supporting material, as with responses to questions. Preferably, the rating includes a quantitative element, such as a binary good/bad or a rating on a scale of 1 to 10. In some embodiments, this rating scale is standardized and required for all ratings.

In a further step 608, the ratings are received and stored in the NPD 100. It will be appreciated from the discussion above that in some embodiments the storing of the rating initiates or is followed by an updating of the of the various rating-types associated with the member whose response is being rated if the rules for those rating-types are such that the rating-type would be effected by the rating.

Some embodiments of an NPD 100 have components to monitor ratings as part of fraud and security mechanisms. For example, such components can identify pairs or groups of members who frequently rate each other or who rate each other unusually highly. Such a component might correlate that information with the profile information of the users in question to identify a common history. Outside the context of ratings, fraud and security components in some embodiments can also detect atypical communication patterns between and among different members, customers, and managers, in some embodiments even analyzing the content of the communications. Some embodiments may use such mechanisms to detect fraud, to comply with regulations, to deliver more statistically relevant results, or to otherwise improve the experience of the NPD 100 to members, customers, and IIV 102 investors.

In some embodiments, a member may also have a profile rating. Some embodiments will rate or stratify members based on their demographic and profile information, such as specialty training, board certification, years in practice, training program, sex, age, race, and practice type (academic vs. private, group vs. solo, multispecialty vs. single specialty, managed care vs. PPO, hospital vs. community based, surgicenter vs. hospital operating theatre, etc.). Some embodiment will further include the ratings of that member's answers, perhaps weighted by the weight of the member assigning that answer. The degree of involvement in the social networking aspects of the NPD 100 is also a factor in the rating in some embodiments. This might include the number of questions answered, the number of questions asked, the number of ratings completed, participation in forums and discussions, and the frequency of profile updates. In the medical context, ratings might incorporate information on updated continuing medical education credits (CME), views of clinical and research articles and information linked to or posted on the NPD 100, participation on the discussion boards and citations to that member's posts, accuracy on any embedded validation questions within surveys, consistency on repeated standardized inter-survey questions provided in sequential surveys, statistical assessment of the members ability to provide predictive value based on her successful predictions on prior surveys, and progressive ranking calibration based on continual inter-physician feedback loops. In an embodiment capable of tracking the activity of a user on the system, the ranking may be affected by the number of informational links a user visits and the amount of time spent on each. For example, if an expert is detected to follow multiple discussions and review posted manuscripts, the expert's ratings may be higher. Analogously, the system may detect a user's behavior and interact with the expert to identify similar resources that might be of interest or to determine if the user's profile should be adjusted to reflect new specializations or knowledge.

Ratings, as well as raw profile information and of course the answers, may factor into the analysis of responses performed by some embodiments. Thus, in some embodiments the responses to a question or survey may be based on both the baseline entry characteristics of the individual expert contributing a response (e.g., that expert's profile information) as well as information from the adaptive expert profile (e.g., that expert's involvement in the community, any evaluations of that involvement, and any evaluations of the experts evaluating that involvement). The analytics may provide a value-weighted, statistical modeling of the pooled responses. In some embodiments, reports including charts and graphs are available. In some embodiments responses to surveys and other questions can be analyzed along a variety of constraints. For example, responses can be analyzed based on the specialties or other properties of the responding experts, can be compared to responses to previous runs of the question, and can be compared to responses to other questions on the survey, other questions flagged as similar by the NPD 100, or other questions otherwise identified for such purposes by the questioner.

Compensation of Member Experts

As discussed above, implementations of an NPD 100 may charges fees from customers or from members. Some embodiments may also monetize ideas generated through the interaction of community members on the NPD, such as by spinning off the product of thought incubators. Some embodiments may also aggregate or otherwise generate presentations of expertise or the ability to generate such presentations and market their availability to third parties or to existing customers who may, for example, have explicitly indicated an interest in some types of information or have previously submitted questions in that area.

In some embodiments, an NPD 100 is affiliated with an IIV 102, which leverages the expertise of the community to inform investment decisions. In some configurations, an IIV 102 might be open to external investors, the NPD 100, members of the expert community, or NPD 100 customers. In some embodiments, the NPD 100 may charge outside investors a fee or be compensated by the IIV 102 for the benefits of being able to use and advertise the affiliation with the NPD 100.

In preferred embodiments, members are compensated based at least in part on their ratings, which, as described above, may be based on their profile, their participation in the NPD 100, and the evaluations of their participation. Compensation may be based on the raw revenue collected by the NPD 100, weighted to take into account a member's rating and the member's direct involvement in realizing that revenue.

In embodiments with an associated IIV 102, compensation may also include shares or fractional shares in the IIV 102 investment vehicle. In some embodiments this type of vested equity is the sole means of member compensation and there is no option to immediately receive payment in the form of currency.

In some embodiments, compensation may deviate from or not follow a standard allocation scheme but instead be based, at least in part, on individualized assessment of the contributions of members. The identities of the members will preferably be kept anonymous from the decision making process.

An example of a compensation scheme that incorporates many of the features discussed in this disclosure is illustrated with the following example. An example NPD 100 has 7 members: 3 male physicians, including one orthopedic specialist, and 4 female physicians, including 2 orthopedic specialists. Customer C1 submits question Q1 for male physicians and agrees to pay $100 for each response. Customer C2 submits question Q2 for all physicians, and agrees to pay $200 for each response. Customer C3 submits question Q3 for orthopedic specialists, agreeing to pay $1,000 for each response. In this example, all physicians respond to all eligible questions. The $300 attributable to C1 is divided among the three male physicians, according to their relative ratings. The $1,400 from C2 is divided among all seven physicians, according to their relative ratings. And the $3,000 from C3 is divided among the three orthopedic specialists, according to their relative ratings.

In general, for each consultation request CR for which a customer 106 has agreed to pay an amount PAYMENT, a member who responded to CR is eligible for a portion of PAYMENT and members who did not or could not respond to CR are not eligible.

In embodiments in which members are compensated in shares, some or all of the compensation to which there are entitled (in this example embodiment, the sum of all the PAYMENTS for which they are eligible weighted, for each PAYMENT, by their relative rating among all the other experts eligible for that PAYMENT) may be distributed as fractional shares of the IIV 102. The number of shares is simply the amount in currency divided by the price-per-share of the shares in the fund.

It will be appreciated that embodiments may implement variations on this allocation scheme by, for example, deferring the allocation of a PAYMENT among the eligible members until all of their responses have been evaluated, so the relative rating of those members can account for this evaluation. Similarly, some embodiments may allocate compensation on a real time basis or near real time basis, while others may allocate compensation according to a schedule or when a threshold of compensation exists to be allocated.

Some embodiments may use the different rating-types discussed above when determining compensation. In the example above, the $1,400 may be divided among the experts according to weightings based at least in part on their general-physician ratings, because it is in part due to their expertise as general physicians that they were targeted. Similarly, the $3,000 allocated to the orthopedic specialists may be allocated according to weightings based at least in part on their relative orthopedic-specialist ratings, which could be quite different from the relative general-physician ratings. Some embodiments may incorporate multiple rating-types in determining an allocation. For example, the above allocations might also take into account C1 and C3 ratings, respectively, where the C1-rating and C3-rating may be based on ratings from users associated with C1 and C3, on ratings of responses to consultation requests from C1 and C3, and on ratings of activity in areas of interest to C1 and C3.

The entire amount of each PAYMENT need not be allocated in this way. For example, some embodiments may set aside some revenue to be allocated at the discretion of the membership or NPD 100 administrators. Embodiments may use such an implementation to compensate members who contribute to the community in ways that are not directly associated with customer requests, such as by serving as administrators, taking leadership roles in community services, or evaluating responses.

In some embodiments, the IIV 102 may pay for consultation requests much as a customer 106 would, and the shares corresponding to that payment can be allocated to community members as described above.

Client Communication Mechanisms and Interfaces

Some embodiments include an application server, preferably secure and including capabilities for targeting mobile computing devices. The application server may, in some embodiments, be a part of the DQS. Users using computing devices such as smart phones, laptop computers, or desktop computers may interface with a client served up by this application server.

Preferred embodiments include a web server, preferably secured. Any client accessing the NPD 100 with a device which supports a compatible web browser may interact with the NPD 100 through the web server.

Other interface servers which are present in some embodiments of the NPD 100 are email and messaging servers (used to push communication to client computing devices or, more generally, to client services which then forward the messages to client devices or retain it for later client access) and interactive voice response servers which allow for interaction over, for example, the telephone.

In some embodiments these client interface servers are supported by or integrated with the DQS, which in some embodiments is accessed directly by client devices. In some embodiments any client interface servers may interact directly with the business rules engine or the other internal components of the NPD 100.

In addition to the question, response, evaluation, and other features described above, in some embodiments the client interface servers present social networking and community functionality, including discussion boards, instant messaging, and libraries of works hosted by the NPD 100 or external works to which the NPD 100 has references.

An NPD 100 may support specialized subcommunities, which forums and features dedicated to the needs of a particular niche. For example, a community of medical experts may have social networking features dedicated to ob-gyns and trauma surgeons. Also, as mentioned above, some embodiments may use thought incubators or make other forms of online collaboration available to members.

Some embodiments may have administrators, community heads, or specialist organizers who coordinate and monitor the activity of these communities. These administrators may be employees of the NPD 100, member volunteers, or members who perform the task in exchange for compensation. In some embodiments, the ratings algorithms may account for administrator feedback on the benefit (or cost) of a member's involvement in a community feature.

Database Structures

In one embodiment, the NPD 100 maintains particular data fields associated with records stored in member, question and answer databases. It will be understood that database tables may be constructed to store virtually limitless data items for any expert member, including demographic and profile information listed above. However, to enable tracking of which expert provided which answer to which question, and to facilitate review of a member's answers, the structures of the database tables for the member, question and answer databases may contain the following fields, among potentially many others.

| Member Database | |
|---|---|
| Field | Type |
| Member Name | Text |
| Member ID | Number |
| Member Rating Factor | Number |

| Question Database | |
|---|---|
| Field | Type |
| Question | Text |
| Question ID | Number |
| Customer ID | Number |

| Answer Database | |
|---|---|
| Field | Type |
| Answer | Text |
| Answer ID | Number |
| Answer Date | Date |
| Question ID | Number |
| Member ID | Number |

In particular embodiments, the NPD 100, through the DQS 206, assigns to each member, upon registration, a unique member ID which, in one embodiment, may begin with 1 (or some other constant such as 1000000) and may be automatically incremented by one for each new member. In similar manner, each new question or other consultation request may be assigned a unique question ID upon introduction into the NPD 100, and each new answer may be assigned a unique answer ID upon introduction into the NPD 100.

The above fields maintained in the member, question and answer database may be used to query, for any member 107 of the NPD 100, a report thoroughly detailing which answers the member provided for each question he or she answered since becoming a member. For example, by using a particular Member ID to query the Answer Database, all answer records that match the Member ID can be retrieved. Then using the Question ID stored in each of those answer records to query the Question Database, the particular question that led to each answer can be retrieved. Thus, in a resulting report, each question and answer can be matched and, using the value of the Answer Date field for each answer record in a sort operation, the questions and answers can be sorted in date order to compile a chronological history of a particular member's contribution.

Figure 7:
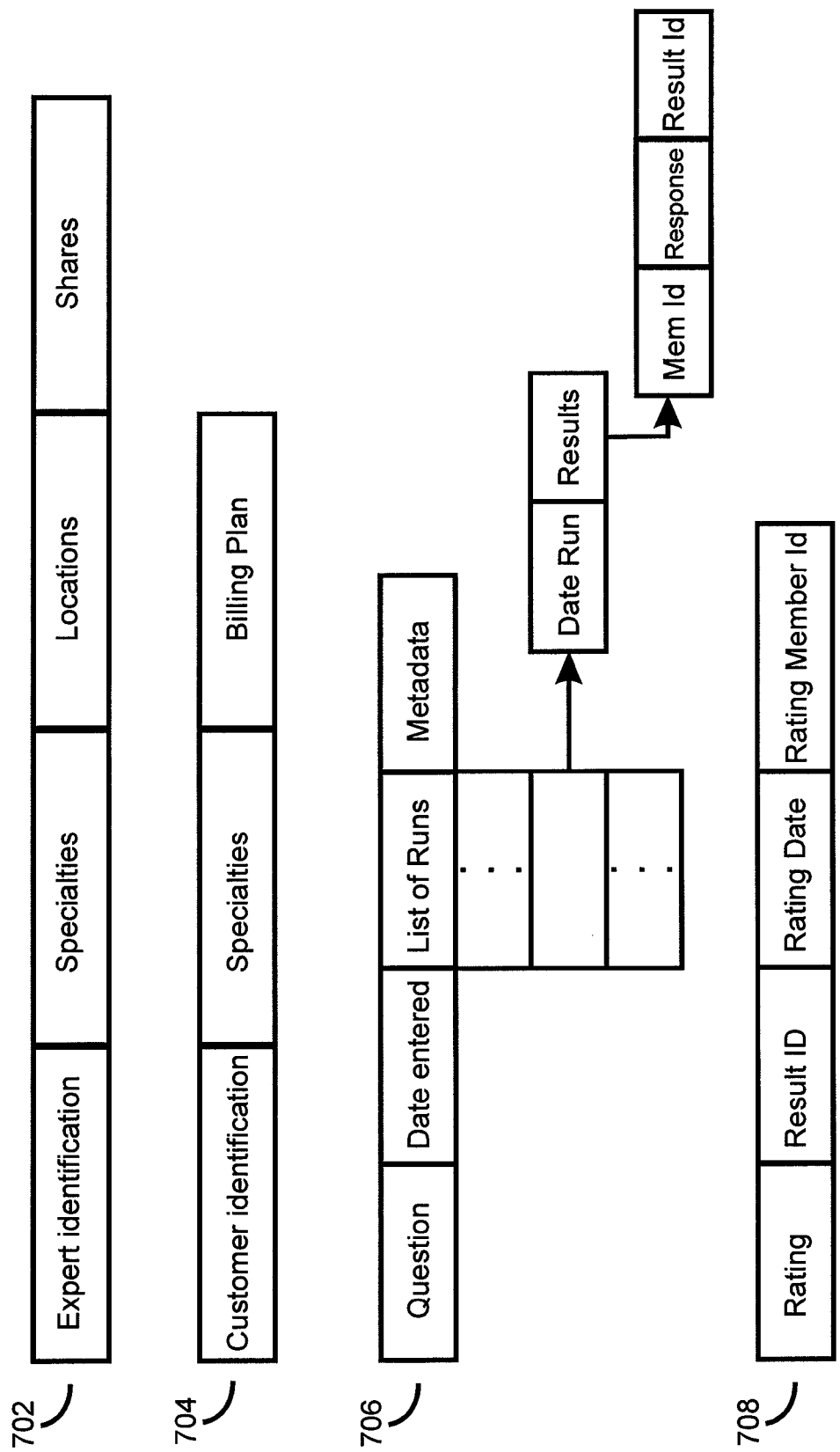
FIG. 7 illustrates categories within which data records may be established and maintained in accordance with some embodiments of the present invention.

The NPD 100 may store and respond to queries for much additional data. As exemplified in FIG. 7, and, in particular, member categories 701, the NPD 100 may track basic and domain specific demographic information including name, address, contact information, specialty areas of training, areas of board certification, years in practice, matriculated training programs, sex, age, race, practice type (including but not limited to academic vs. private, group vs. solo, multispecialty vs. single specialty, managed care vs. PPO, hospital vs. community based, surgi-center vs. hospital operating theatre, geographic region of practice, and geographic region of training), peer-based entry ranking, current and prior participation in advisory boards, involvement in pharmaceutical consultation, participation in clinical trials (for example, NIH, pharmaceutical, or investigator sponsored). It also includes information on publications, continuing education, and business and research affiliations.

Those of ordinary skill will appreciate that the NPD 100 uses the appropriate datatype for each of these fields and appropriate techniques for avoiding, for example, confusion between null values and 0 values. For instance, most of the above records would be text or string type values, with information such as years in practice perhaps being implemented as two fields: one a binary field indicating whether the expert does practice and the second an integer or decimal indicating the amount of time (or, in other embodiments, the date the expert began practicing). Fields which may have multiple values may be normalized using auxiliary tables. In a typical embodiment, each customer records is also augmented with a unique member ID that is used to associate other internal records with the member. In some embodiments, the member record may include dynamically generated information such as the member's shares or ratings.

With regard to customer information, customer categories 702 include information tracking a customer's billing plan. In one embodiment, the customer's name and address information are strings, and the system generates a unique long integer to identify the customer internally. As discussed, the billing plan may be a sophisticated scheme that takes into account information such as the number and frequency of questions, the panel or target audience for the questions, and the number of users who may be associated with the customer. Thus the billing plan field may be a reference to another table containing detailed billing terms. The NPD 100 may also track the actual users associated with a customer by tracking, for example, basic information such as name and contact information in string fields, and include for each such user a reference back to the record of the customer with which the user is affiliated.

Question categories 703 illustrate data that the NPD 100, in one embodiment, may track associated with questions. Along with the question itself, stored in a string field, the record includes auditing information about the date entered (in a timestamp field); the source of the question (a reference to a user, a member, or a customer, for example); any metadata generated by the system or the user, such as what discussion board, if any, the question came from or what specialties it pertains to (references to records in other tables); and a list of runs of the question (references to records in a table of runs). Each run corresponds to a record with an identifier for that run, a reference to the question record, and a timestamp indicating when the run occurred. An association between a run and the members from whom responses were solicited may be maintained by, for example, a member-run association table that associates member-IDs with run-IDs. Each run record is also associated with results records and each results records is also associated with a member. One implementation includes a run-results that includes the text of the result in a string field, a reference to a result record, a reference to the member who provided the result, a timestamp field, and a result-ID. It may also include system metadata such as when it was entered and the means by which it was entered.

Each result may also be associated with one or more evaluations via a results-evaluations table where each records includes a result-ID, the substance of the evaluation, references to any other records containing supporting information for the evaluation, and a reference to the member who provided the evaluation. Rating categories 704 illustrate data that the NPD 100 may track that is associated with ratings of members, such as the rating text, a result ID corresponding to an answer or result being rated, the date of the rating and the member identification number for the rating member. It will be appreciated that database records may be store and track these and other criteria and information associated with ratings.

Following from the above description, implementations of storage structures for tracking of the various entities and associations (such as evaluations of participation in NPD 100 discussion boards) the maintaining and evaluating of publications, and surveys, should be readily apparent to one of ordinary skill in the art.

Server

Figure 8:
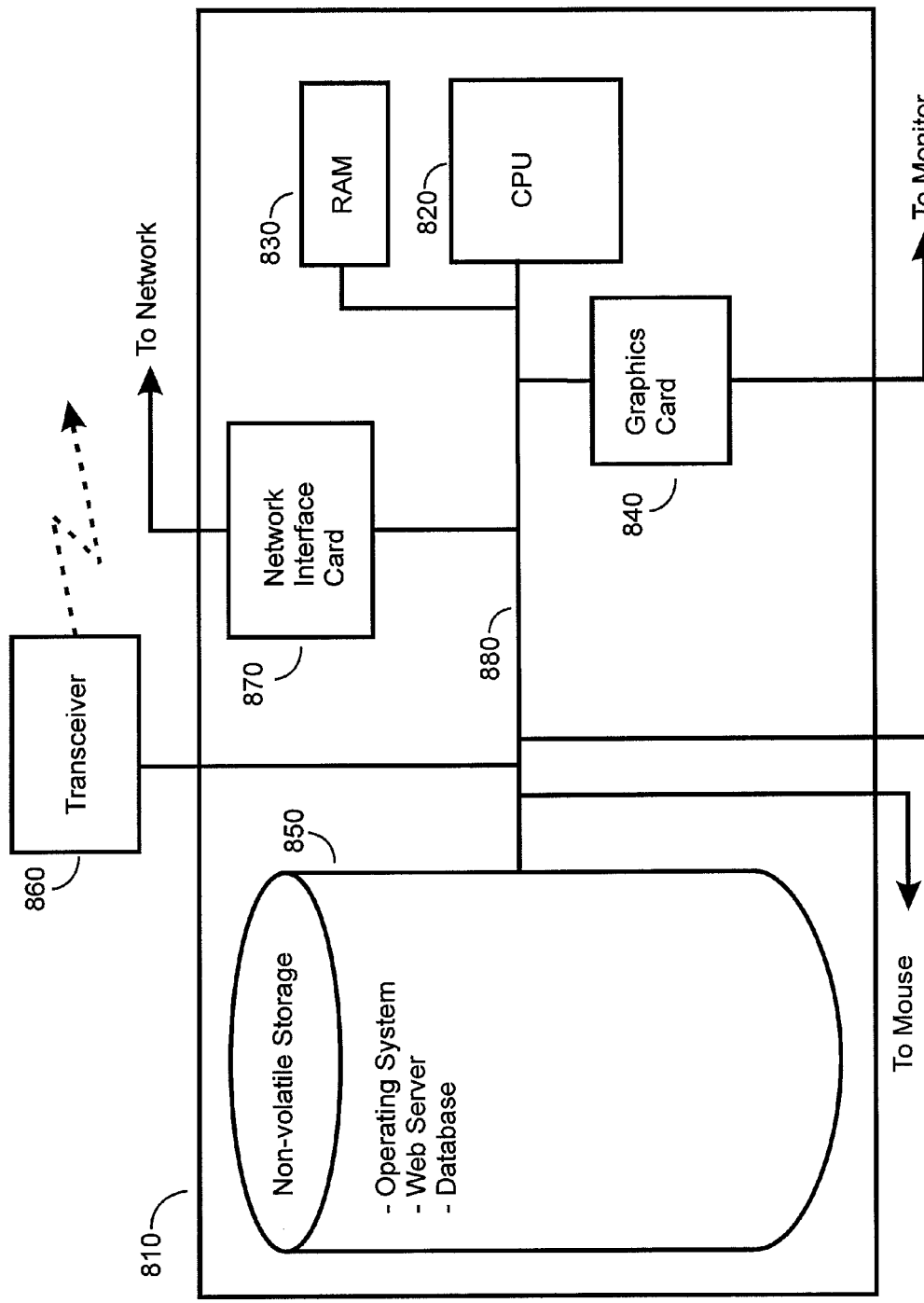
FIG. 8 illustrates components of a server computing system in one embodiment of the preset invention.

FIG. 8 illustrates additional descriptive information for one embodiment of a server 810 that may be used with the present invention. The server 810 includes a cpu 820, a RAM (random access memory) 830, a graphics card 840, a non-volatile storage 850, a transceiver 860, a network interface card 870, and a bus 880 that interconnects the components. The cpu 820 may be any of a number of available commercial cpu units, including those available from Intel (core 2 duo, core i7, etc.) or from AMD (athlon, opteron, etc.) and may be single- or multi-core. The RAM 830 may preferably constitute at least 3 GB of storage, but may be more or less, and may be comprised of three 1 GB modules. The graphics card 840 may be an NVIDIA Geforce graphics processing module, or another graphics card sufficient to generate graphical user interface displays such as those generated by standard web browsers, including Microsoft Internet Explorer, or Mozilla Firefox. The non-volatile storage 850 may be a hard disk drive, solid state drive or other non-volatile storage, preferably providing 40 GB of storage, but may provide more or less. The transceiver 860 may be a D-Link or NetGear transceiver or wireless router which provides for network access without the need for a cable. The transceiver 860 generally includes a buffer capable of receiving packets of data, wherein each packet includes address information and payload content. The network interface card 870 may provide 10 Mbps of throughput (or more or less) on a LAN connection and may provide an Ethernet connection port. The server 810 may also include connections for mouse, keyboard and monitor (not shown).

In operation, the server 810 may run software by loading the relevant instructions for processing by the CPU 820. Software may be stored on the non-volatile storage 850, including an operating system, such as Windows, Unix or Linux, a web server such as apache, a web browser such as Internet Explorer, and a database such as MySQL or Oracle. The server 810 may also store template web pages, coded in HTML, to be transmitted when requested by a browser, and the template web pages may include scripts (such as PERL scripts) and queries to particular content stored in the database so that web pages may be generated for transmission with certain dynamic content retrieved from the database prior to transmission. The server may also run NPD components and/or IIV components as described above, and may be accessed by members, customers, administrators and/or IIV managers.

Client

FIG. 9 illustrates additional information describing one embodiment of a client mobile device 910 that may be used with the present invention. The mobile device 910 includes a CPU 915, a RAM 920, a display interface 925, a non-volatile storage 930, a transceiver 935, a touchscreen controller 940, a baseband processor 945, a power management module 950, a battery charge module 955, a GPS 960, and an accelerometer 965. In embodiment, the mobile device 910 may be an Apple iPhone, which includes such components. In other embodiments, the mobile device may be a Blackberry by RIM, or another mobile device that may access the Internet wirelessly or via a cable, such as a laptop, netbook, PDA or a smartphone.

The mobile device 910, in one embodiment, may run software including an operating system and a web browser. The mobile device 910 may also include, stored in non-volatile storage 930, authentication information, possibly in a database, that uniquely identifies a member 107, a customer 106, an administrator 101, or an IIS manager 103. Using a web browser function, the mobile device 910 may request access to a domain name associated with the NPD server, such as, for example, www.npd.com. The NPD server then, through the DQS 206, may register or authenticate the member, manager, customer or administrator accessing the NPD with the mobile device 910.

Registration

FIG. 10 shows a sample registration form that a user completes when becoming a member. In some embodiments, a member uses a similar form to update her membership details.

In addition to prompting for demographic and contact information, the form allows the user to indicate one or more practice areas and specialties with controls 1001. Using controls 1002 the user can indicate the degree and type of engagement she'd like to have with the community. This may influence the types of questions she receives and the level of compensation, for example. The form allows the user to upload a CV using control 1003 and to upload or link to publications using control 1004. As an example of how a form can solicit information about conflicts, control 1005 prompts the user to enter information about funding sources and employers. Control area 1006 permits the user to enter personal information such as name and contact information. In some configurations, this may be put to other purposes, such as enhancing the social networking functions of the configuration.

Registration may require private information. For example, a community of medical experts may require Federal DEA number (Drug Enforcement Agency), State Medical License Number, Social Security Number (IRS information for payment processing), home address, business address, medical school matriculation (for verification of active medical licensing), and similar information. In some embodiments, the NPD 100 may verify or authenticate this information by, for example, accessing public or private database, routing confirmation requests to referenced individuals or entities, or seeking to confirm the information by mining public information or information already available to the NPD 100.

Registration Interface

As noted in the detailed descriptions above, embodiments may interact with customers in diverse ways and different embodiments require and use different information. The form in FIG. 11 illustrates one example of a customer registration form. Using control 1101, a user at the customer, or in some embodiments, an agent affiliated with the NPD 100, enters information about the customer such as basic contact and demographic information. Optionally, information about authorized users affiliated with the customer may be entered at this point. In some embodiments, such information can be added later, by the customer.

Using control 1102, the user selects from a number of predefined billing plans or indicates that a custom plan has been arranged. In some embodiments, such a custom plan would be documented and described elsewhere in the NPD 100 and any components responsible for validating the behavior of the NPD 100 ensure adherence with the terms of the plan. Control 1103 allows for the specification of a payment plan. This illustrated embodiment shows currency and security options, but some embodiments may support only one of those, additional mechanisms, or a combination of payment mechanisms.

Finally, control 1104 allows the client to specify any affiliated entities. This can be used by the NPD 100 for marketing purposes, and also for conflict check and auditing purposes.

Customer registration may also allow for entry of particular areas of interest, which is an example of a piece of information an embodiment might use to provide automated updates on the available of information or experts that might be of interest to the customer.

Create Consultation Request

As discussed above, some embodiments process a wide variety of interactions with the NPD 100 as questions and responses. For example, although a member may appear to be participating in a message board or engaging in a chat with a fellow community member, some embodiments will store the communications as a collection of questions and responses, tagging the data based on its contents, the participants, and the forum in which they are participating.

However, in some embodiments users can explicitly ask questions. For example, customers may wish to conduct surveys. FIG. 12 shows a sample form which some embodiments might use for such purposes.

Using control 1201 and its associated controls, the customer enters a question and provides links to associated documents, metatags, or options to constrain the responses.

Using control 1202 and its associated controls, the customer can refine its target audience. In some embodiments, targeting is suggested by the system.

Control 1203 determines anonymity. It may be that in certain contexts a questioner is required or prefers to disclose an identity and this control allows that to occur.

Controls 1204 and 1205 allow the customer to set a deadline for responses and to set a date for when solicitation of responses should commence. In some embodiments, these controls are more sophisticated and allow for establishing a series of repeated runs or surveys.

Although specific embodiments have been disclosed, other embodiments that are apparent to those of ordinary skill in the art, including embodiments which do not provide all of the benefits and features set forth herein, are also within the scope of this disclosure. The foregoing description of preferred implementations or embodiments has been presented by way of example only, and should not be read in a limiting sense. Accordingly, the scope of protection is defined only by reference to the appended claims.

The inventions described herein may be embodied in other specific forms without departing from the essential characteristics as described herein. The embodiments described above are to be considered in all respects as illustrative only and not restrictive any manner, including extension into non-physician or medical arenas. For example, any platform in any field or sub-field that exploits rapid survey interaction from a group of established invested end-users shall be included in this patent claim.

What is claimed is:

1. A computer system for managing consultation requests comprising:
   at least one processor;
   a first storage in communication with the at least one processor, wherein first and second rating values are stored in the first storage;
   a first communication port in communication with the at least one processor, wherein the first communication port is configured to receive first data representing a consultation request, and wherein first software instructions are executed by the at least one processor to process the first data and to send second data representing the consultation request to first and second reviewers;
   a second communication port in communication with the at least one processor, wherein the second communication port is configured to receive third data representing a response to the consultation request provided by the first reviewer and is also configured to receive fourth data representing a response to the consultation request provided by the second reviewer, and wherein second software instructions are executed by the at least one processor to process the third and fourth data and to send to a requestor fifth data representing the responses to the consultation request provided by the first and second reviewers; and
   a third communication port in communication with the at least one processor, wherein the third communication port is configured to receive sixth data representing a payment value corresponding to the value of the responses represented by the fifth data, wherein third software instructions are executed by the at least one processor to process the sixth data, to combine a value represented by the sixth data with seventh data representing the value of an account of which each of the first and second reviewers owns a fractional share to calculate a modified account value, to calculate a modified fractional share of the account owned by the first reviewer based on the first rating value, and to calculate a modified fractional share of the account owned by the second reviewer based on the second rating value.

2. The computer system as described in claim 1 wherein the first, second and third communication ports are the same communication port.

3. The computer system as described in claim 1 wherein the first, second and third software instructions are stored on the first storage.

4. The computer system as described in claim 1 wherein the first communication port is further configured to receive eighth data representing rating information provided by a third reviewer, and wherein fourth software instructions are executed by the at least one processor to process the eighth data and to modify the first rating value based on the rating information represented by the eighth data.

5. The computer system as described in claim 1 wherein the account comprises one or more investments.

6. The computer system of claim 5, wherein the first and second reviewers are experts in a particular field and the one or more investments are in at least one market sector within the particular field.

7. A method for processing consultation requests comprising the steps of:
   sending a first consultation request to first and second experts;
   receiving first answers in response to the first consultation request from the first and second experts;
   accessing a first rating that is associated with the first expert and that depends, at least in part, on at least one of the first answers;
   accessing a second rating that is associated with the second expert and that depends, at least in part, on at least one of the first answers;
   receiving a payment value corresponding to a value of at least some of the first answers;
   combining the payment value with the value of an asset to calculate a modified value of the asset; and
   calculating, by at least one computer processor, a first fractional ownership in the asset based on the first rating, the first fractional ownership owned by the first expert; and calculating a second fractional ownership in the asset based on the second rating, the second fractional ownership owned by the second expert.

8. The method of claim 7, comprising the further step of sending the first answers to a customer.

9. The method of claim 8, comprising the further steps of:
sending a second consultation request to the first expert and a third expert;
receiving second answers in response to the second consultation request from the first and third experts;
accessing a third rating that is associated with the first expert and that depends, at least in part, on at least one of the second answers; and
calculating a third fractional share ownership in a second asset based on the third rating, the third fractional share ownership owned by the first expert.

10. The method of claim 9, wherein the third rating differs from the first rating.

11. The method of claim 9, comprising the further step of:
accessing a fourth rating that is associated with the third expert and that depends, at least in part, on at least one of the second answers; and
calculating a fourth fractional share ownership in the second asset based on the fourth rating, the fractional share ownership owned by the third expert.

12. The method of claim 9, comprising the further step of:
sending the second answers to a customer; and
receiving a second payment, wherein the value of the second asset is based, at least in part, on a value of the second payment.

13. The method of claim 11, wherein the first and the second asset are the same asset.

14. The method of claim 7, wherein said calculating is automated.

15. The method of claim 7, wherein the asset comprises one or more investments.

16. The method of claim 7, wherein the first and second experts are experts in a particular field, and the one or more investments are in at least one market sector within the particular field.

17. A method for processing consultation requests comprising the steps of:
sending a first consultation request to first and second experts;
receiving answers in response to the first consultation request from the first and second experts;
accessing a first rating associated with the first expert and that is based, at least in part, on an analysis of at least a first set of information about the first expert;
accessing a second rating associated with the second expert and that is based, at least in part, on an analysis of at least a first set of information about the second expert;
receiving a payment from a customer, wherein the value of the payment corresponds to a value of at least some of the answers;
combining the value of the payment with the value of an asset to calculate a modified value of the asset;
calculating, by at least one computer processor, a first fractional ownership in the asset based on at least the first rating associated with the first expert and the payment, the first fractional ownership owned by the first expert: and
calculating a second fractional ownership in the asset based on at least the second rating associated with the second expert and the payment, the second fractional ownership owned by the second expert.

18. The method of claim 17, comprising the further step of sending the received answers to a customer.

19. Computer readable media having computer readable instructions recorded thereon for processing consultation requests, the instructions comprising:
instructions for sending a first consultation request to first and second experts;
instructions for receiving first answers in response to the first consultation request from the first and second experts;
instructions for accessing a first rating associated with the first expert;
instructions for accessing a second rating associated with the second expert;
instructions for receiving a payment, the value of the payment corresponding to a value of at least some of the first answers;
instructions for combining the payment value with the value of an asset to calculate a modified value of the asset; and
instructions for calculating, by one or more computer processors, a first fractional ownership in the asset based on the first rating, the first fractional ownership owned by the first expert, and a second fractional ownership in the asset based on the second rating, the second fractional ownership owned by the second expert.

20. The computer readable media of claim 19, the instructions further comprising:
instructions for sending the first answers to a customer.

21. The computer readable media of claim 20, the instructions further comprising:
instructions for sending a second consultation request to the first expert and a third expert;
instructions for receiving second answers in response to the second consultation request from the first and third experts;
instructions for accessing a third rating, the third rating associated with the first expert and that is based, at least in part, on an analysis of at least one of the second answers; and
instructions for calculating a third fractional share ownership in a second asset based on the third rating, the third fractional share ownership owned by the first expert.

22. The computer readable media of claim 21, the instructions further comprising:
instructions for accessing a fourth rating, the fourth rating associated with the third expert and that is based, at least in part, on an analysis of at least one of the second answers; and
instructions for calculating a fourth fractional share ownership in the second asset based on the fourth rating, the fourth fractional share ownership owned by the third expert.

23. The computer readable media of claim 21, the instructions further comprising:
instructions for sending the second answers to a customer; and
instructions for receiving a second payment, wherein the value of the second asset is based, at least in part, on a value of the second payment.

24. The computer readable media of claim 22, wherein the first asset and the second asset are the same asset.

25. The computer readable media of claim 21, wherein the third rating differs from the first rating.

26. The computer readable media of claim 19, wherein the calculation of the first fractional ownership share is automated.

27. Computer readable media having computer readable instructions recorded thereon for processing consultation requests, the instructions comprising:
- instructions for sending a first consultation request to first and second experts;
- instructions for receiving answers in response to the first consultation request from the first and second experts;
- instructions for accessing a first rating associated with the first expert and that is based, at least in part, on an analysis of at least a first set of information about the first expert;
- instructions for accessing a second rating associated with the second expert and that is based, at least in part, on an analysis of at least a first set of information about the second expert;
- instructions for receiving a payment from a customer, wherein the value of the payment corresponds to a value of at least some of the first answers;
- instructions for combining the value of the payment with the value of an asset to calculate a modified value of the asset; and
- instructions for calculating, by one or more computer processors, a first fractional ownership in the asset based on at least the first rating associated with the first expert and the payment, the first fractional ownership owned by the first expert, and a second fractional ownership in the asset based on at least the second rating associated with the second expert and the payment, the second fractional ownership owned by the second expert and wherein the value of the asset includes the value of the payment.

28. The computer readable media of claim 27, the instructions further comprising instructions for sending the received answers to a customer.

* * * * *